US009895149B2

(12) United States Patent
Johnson et al.

(10) Patent No.: US 9,895,149 B2
(45) Date of Patent: Feb. 20, 2018

(54) MAGNETICALLY ACTIVATED ARTERIOVENOUS ACCESS VALVE SYSTEM AND RELATED METHODS

(71) Applicant: DIAXAMED, LLC, Raleigh, NC (US)

(72) Inventors: James S. Johnson, Greenville, SC (US); Frank V. Patterson, Exeter, NH (US); Jordan Jacobs, Randolph, MA (US)

(73) Assignee: DIAXAMED, LLC, Raleigh, NC (US)

( * ) Notice: Subject to any disclaimer, the term of this patent is extended or adjusted under 35 U.S.C. 154(b) by 444 days.

(21) Appl. No.: 14/695,241

(22) Filed: Apr. 24, 2015

(65) Prior Publication Data

US 2015/0305746 A1   Oct. 29, 2015

Related U.S. Application Data

(60) Provisional application No. 61/984,550, filed on Apr. 25, 2014.

(51) Int. Cl.
*A61M 5/00* (2006.01)
*A61B 17/11* (2006.01)
(Continued)

(52) U.S. Cl.
CPC ........ *A61B 17/11* (2013.01); *A61B 17/12045* (2013.01); *A61B 17/12136* (2013.01);
(Continued)

(58) Field of Classification Search
CPC .............. A61B 17/11; A61B 17/12045; A61B 17/12136; A61B 2017/1107;
(Continued)

(56) References Cited

U.S. PATENT DOCUMENTS 3,730,186 A    5/1973   Edmunds, Jr. et al.
3,998,222 A    12/1976  Shihata
(Continued)

FOREIGN PATENT DOCUMENTS

DE          29513195        12/1996
WO          03/000314       1/2003
WO      WO 2009/046408 A1   4/2009

OTHER PUBLICATIONS

Brandon J. Hopkins et al., Hemodialysis Graft Resistance Adjustment Device, Journal of Medical Devices, vol. 6, Jun. 2012, 6 pages.
(Continued)

*Primary Examiner* — Philip R Wiest
(74) *Attorney, Agent, or Firm* — Dority & Manning, P.A.

(57) ABSTRACT

In one aspect, an arteriovenous access valve system may generally include a first valve configured to be positioned at or adjacent to an end of an arteriovenous graft and a second valve configured to be positioned at or adjacent to an opposite end of the arteriovenous graft. In addition, the system may include an actuator assembly in fluid communication with the first and second valves. The actuator assembly may include a housing, a driver assembly positioned within the housing and a drive magnet positioned within the housing. The drive magnet may be rotatably coupled to the driver assembly such that, when the drive magnet is rotated, the driver assembly is configured to be rotatably driven so as to supply fluid to the first and second valves or to draw fluid out of the first and second valves depending on a rotational direction of the driver assembly.

19 Claims, 25 Drawing Sheets

(51) Int. Cl.
  *A61F 2/06* (2013.01)
  *A61B 17/12* (2006.01)
  *A61M 1/36* (2006.01)
  *A61B 17/00* (2006.01)
  *A61B 90/00* (2016.01)

(52) U.S. Cl.
  CPC .......... *A61F 2/064* (2013.01); *A61M 1/3655* (2013.01); *A61B 2017/00115* (2013.01); *A61B 2017/00411* (2013.01); *A61B 2017/00539* (2013.01); *A61B 2017/1107* (2013.01); *A61B 2017/1139* (2013.01); *A61B 2090/0807* (2016.02); *A61F 2002/068* (2013.01); *A61M 2205/3331* (2013.01); *A61M 2205/3523* (2013.01)

(58) Field of Classification Search
  CPC .. A61B 2017/1139; A61B 2017/12045; A61B 2017/00115; A61B 2017/00411; A61B 2017/00539; A61B 2090/0807; A61F 2/064; A61F 2002/068; A61M 1/3655; A61M 2205/3331; A61M 2205/3523
  USPC .......................................................... 604/8, 9
  See application file for complete search history.

(56) References Cited

U.S. PATENT DOCUMENTS

| | | |
|---|---|---|
| 4,464,164 A | 8/1984 | Troutner et al. |
| 4,486,189 A | 12/1984 | Troutner et al. |
| 4,822,341 A | 4/1989 | Colone |
| 4,828,544 A | 5/1989 | Lane et al. |
| 5,024,668 A | 6/1991 | Peters et al. |
| 5,034,265 A | 7/1991 | Hoffman et al. |
| 5,336,181 A | 8/1994 | Nakao et al. |
| 5,562,617 A | 10/1996 | Finch, Jr. et al. |
| 5,662,608 A | 9/1997 | Imran et al. |
| 5,713,859 A | 2/1998 | Finch, Jr. et al. |
| 5,797,879 A | 8/1998 | DeCampli |
| 5,879,320 A | 3/1999 | Cazenave |
| 5,919,369 A | 7/1999 | Ash |
| 5,924,448 A | 7/1999 | West |
| 5,976,178 A | 11/1999 | Goldsteen et al. |
| 6,019,788 A | 2/2000 | Butters et al. |
| 6,053,891 A | 4/2000 | DeCampli |
| 6,053,901 A | 4/2000 | Finch, Jr. et al. |
| 6,056,717 A | 5/2000 | Finch et al. |
| 6,086,553 A | 7/2000 | Akbik |
| 6,090,067 A | 7/2000 | Carter |
| 6,102,884 A | 8/2000 | Squitieri |
| 6,319,465 B1 | 11/2001 | Schnell et al. |
| 6,348,162 B1 | 2/2002 | Ash |
| 6,352,521 B1 | 3/2002 | Prosl |
| 6,582,409 B1 | 6/2003 | Squitieri |
| 6,595,941 B1 | 7/2003 | Blatter |
| 6,648,873 B2 | 11/2003 | Arenberg et al. |
| 6,656,151 B1 | 12/2003 | Blatter |
| 6,988,983 B2 | 1/2006 | Connors et al. |
| 7,025,741 B2 | 4/2006 | Cull |
| 7,074,178 B2 | 7/2006 | Connors et al. |
| 7,223,257 B2 | 5/2007 | Shubayev et al. |
| 7,762,977 B2 | 7/2010 | Porter et al. |
| 8,114,044 B2 | 2/2012 | Cull |
| 8,460,253 B2 | 6/2013 | Dugrot |
| 8,551,033 B1 | 10/2013 | Batiste |
| 9,764,698 B2 | 9/2017 | Cho |
| 2003/0014003 A1 | 1/2003 | Gertner |
| 2004/0168969 A1 | 9/2004 | Sternby et al. |
| 2006/0064159 A1 | 3/2006 | Porter et al. |
| 2006/0079827 A1 | 4/2006 | Jensen et al. |
| 2006/0224100 A1 | 10/2006 | Gertner |
| 2007/0249987 A1 | 10/2007 | Gertner |
| 2008/0300528 A1 | 12/2008 | Cull |
| 2009/0030498 A1 | 1/2009 | Cull |
| 2011/0060264 A1 | 3/2011 | Porter et al. |
| 2011/0130702 A1 | 6/2011 | Stergiopulos |
| 2013/0303959 A1 | 11/2013 | Cull |
| 2014/0236063 A1 | 8/2014 | Cull |

OTHER PUBLICATIONS

Search Report and Written Opinion for PCT/US2004/10209.
International Search Report for PCT/US2009/055671, 4 pages.
International Search Report for PCT/US2012/056611.
International Search Report for PCT/US2015/027418, 12 pages.
Vestiflo Advanced Pelvic Health inFlow Restoring Control, Intraurethral Valve-Pump and Activator, Non-Surgical Urinary Prosthesis for Women, Instructions for Physician Use. (10 pages).
Vestiflo Advanced Pelvic Health inFlow Urinary Prosthesis. 2015-2016 (5 pages).
InFlow Restoring Control How the inFlow Works 2015-2016 (3 pages).
InFlow Restoring Control The inFlow Urinary Prosthesis for Women with IDC. 2015-2016 (12 pages).
InFlow Restoring Control Device and Activator Information for Patients and Instructions for Use. Sep. 2016 (10 pages).
PCT/US2015/027418 European International Search Report, Dated Nov. 29, 2017 (8 pages).

MAGNETICALLY ACTIVATED ARTERIOVENOUS ACCESS VALVE SYSTEM AND RELATED METHODS

CROSS-REFERENCE TO RELATED APPLICATIONS

This application is based upon and claims priority to U.S. Provisional Patent Application No. 61/984,550, filed on Apr. 25, 2014 and entitled "Magnetically Activated Ateriovenous Access Valve System and Related Methods," which is hereby incorporated by reference herein in its entirety.

FIELD OF THE INVENTION

The present subject matter relates generally to arteriovenous access valve systems and, more particularly, to a needle-free, magnetically activated valve system for opening and closing valves positioned at or adjacent to the ends of an arteriovenous graft.

BACKGROUND OF THE INVENTION

The function of kidneys, which are glandular organs located in the upper abdominal cavity of vertebrates, is to filter blood and remove waste products. Specifically, kidneys separate water and waste products of metabolism from blood and excrete them as urine through the bladder. Chronic renal failure is a disease of the kidney in which the kidney function breaks down and is no longer able to filter blood and remove waste substances. Should certain toxic waste substances not be removed from the blood, the toxic substances may increase to lethal concentrations within the body.

Hemodialysis is a life-sustaining treatment for patients who have renal failure. Hemodialysis is a process whereby the patient's blood is filtered and toxins are removed using an extracorporeal dialysis machine. For hemodialysis to be effective, large volumes of blood must be removed rapidly from the patient's body, passed through the dialysis machine, and returned to the patient. A number of operations have been developed to provide access to the circulation system of a patient such that patients may be connected to the dialysis machine.

For example, a commonly performed hemodialysis access operation is a subcutaneous placement of an arteriovenous graft, which is made from a biocompatible tube. The biocompatible tube can be made of, for instance, a fluoropolymer such as polytetrafluoroethylene. One end of the tube is connected to an artery while the other end is connected to a vein. The arteriovenous graft is typically placed either in the leg or arm of a patient.

Blood flows from the artery, through the graft and into the vein. To connect the patient to a dialysis machine, two large hypodermic needles are inserted through the skin and into the graft. Blood is removed from the patient through one needle, circulated through the dialysis machine, and returned to the patient through the second needle. Typically, patients undergo hemodialysis approximately four hours a day, three days a week.

Various problems, however, have been experienced with the use of an arteriovenous graft. For example, arterial steal occurs when excessive blood flow through the arteriovenous graft "steals" blood from the distal arterial bed. Arterial steal can prevent the proper supply of blood from reaching the extremity of a patient.

To address such problems, systems and processes have been deployed which can minimize or prevent complications by closing the arteriovenous graft when hemodialysis is not taking place. An example of one such system is described in U.S. Pat. No. 7,025,741 entitled "Arteriovenous access valve system and process", which is hereby incorporated by reference herein in its entirety for all purposes. These systems and processes utilize valves, such as balloon valves, to force closure of one or more portions of an arteriovenous graft by pressing the arteriovenous graft walls together.

However, such implanted valve systems typically require that the valves be actuated using one or more hypodermic needles. For example, for a system including two balloon valves (e.g., a valve positioned at each end of the arteriovenous graft), two separate needles must be used inserted through the patient's skin and into corresponding injection ports associated with the valves to allow the balloons to be inflated and deflated. The use of such needles significantly adds to the ongoing costs of performing hemodialysis processes. In addition, the needles add to the discomfort level of the patient as the hemodialysis process is being performed.

Accordingly, a needle-free, arteriovenous access valve system would be welcomed in the technology.

BRIEF DESCRIPTION OF THE INVENTION

Aspects and advantages of the invention will be set forth in part in the following description, or may be obvious from the description, or may be learned through practice of the invention.

In one aspect, the present subject matter is directed to an arteriovenous access valve system. The system may generally include a first valve configured to be positioned at or adjacent to an end of an arteriovenous graft and a second valve configured to be positioned at or adjacent to an opposite end of the arteriovenous graft. In addition, the system may include an actuator assembly in fluid communication with the first and second valves. The actuator assembly may include a housing, a driver assembly positioned within the housing and a drive magnet positioned within the housing. The drive magnet may be rotatably coupled to the driver assembly such that, when the drive magnet is rotated, the driver assembly is configured to be rotatably driven so as to supply fluid to the first and second valves or to draw fluid out of the first and second valves depending on a rotational direction of the driver assembly.

In another aspect, the present subject matter is directed to an arteriovenous access valve system. The system may generally include a first valve configured to be positioned at or adjacent to an end of an arteriovenous graft and a second valve configured to be positioned at or adjacent to an opposite end of the arteriovenous graft. The system may also include an actuator assembly in fluid communication with the first and second valves. The actuator assembly may include a housing and a driver assembly positioned within the housing. In addition, the system may include an activator device having an activator magnet. The activator device may be configured to rotate the activator magnet so as to rotationally drive the driver assembly. Moreover, the driver assembly may be configured to supply fluid to the first and second valves or draw fluid out of the first and second valves depending on a rotational direction at which the driver assembly is being driven.

In a further aspect, the present subject matter is directed to a method for operating an arteriovenous access valve system that includes an implemented actuator assembly in fluid communication with first and second valves. The method may generally include positioning an external activator device in proximity to the implanted actuator assembly, wherein the external activator device includes a rotatable magnet. In addition, the method may include rotating the magnet while the external activator device is positioned adjacent to the implanted actuator assembly so as to rotationally drive a driver assembly of the implanted actuator assembly. The driver assembly may be configured to supply fluid to the first and second valves or draw fluid out of the first and second valves depending on a rotational direction at which the driver assembly is being driven.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION OF THE INVENTION

Figure 1:
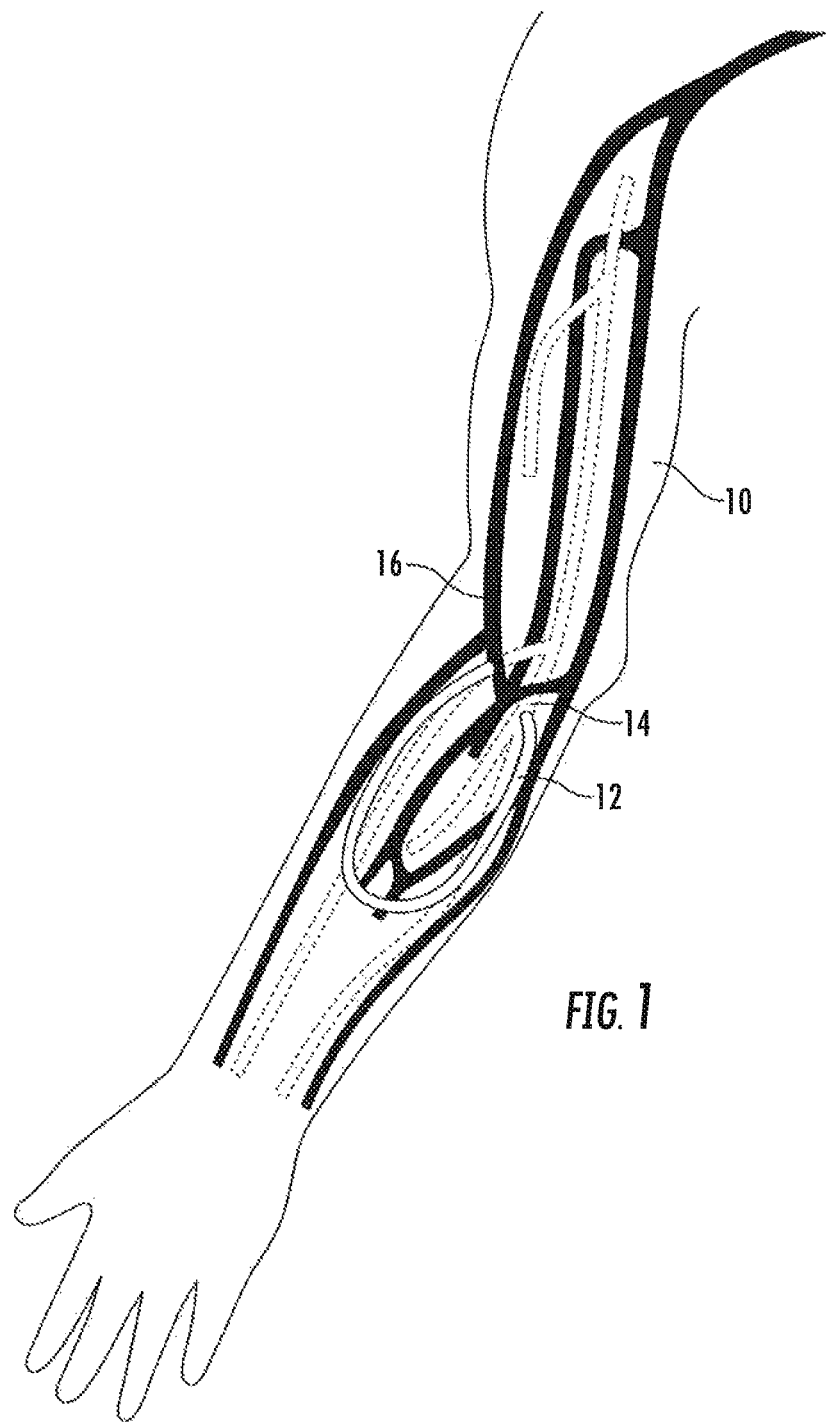
FIG. 1 illustrates a side view with cut away portions of a human arm illustrating one example of the placement of an arteriovenous graft.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to a magnetically activated arteriovenous access valve system. Specifically, in several embodiments, the system may include a subcutaneously implanted actuator assembly in fluid communication with fluid actuated valves (e.g., balloon valves) positioned at each end of an arteriovenous graft. In addition, the system may include an external activator device configured to activate the actuator assembly using magnetic forces. For example, as will be described below, the activator device may include a motor configured to rotate one or more magnets contained within the device both clockwise and counter-clockwise. By placing the activator device adjacent to the location of the implanted actuator assembly, rotation of the magnet(s) may activate a driver assembly of the actuator assembly (e.g., a screw drive or a gear pump), thereby causing fluid to be delivered to and/or drawn away from the balloon valves. For instance, by rotating the magnet(s) in a first direction, the driver assembly may be configured to supply fluid into the balloons associated with the valves in order to close the valves and prevent blood from flowing through the graft. Similarly, by rotating the magnet(s) in the opposite direction, the driver assembly may be configured to draw fluid out of the balloons in order to open the valves and allow blood to flow through the graft.

Additionally, in several embodiments, one or more pressure sensors may be incorporated into the disclosed system, such as by positioning the pressure sensor(s) within the actuator assembly and/or by associating the pressure sensor(s) with the valves and/or the tubing connecting the actuator assembly to the valves. The pressure sensor(s) may generally be configured to read the pressure of the fluid contained within the system between the driver assembly and the valves, thereby providing an indication of the inflation/deflation level of each balloon. For instance, as will be described below, the system may, in one embodiment, include two pressure sensors, with each pressure sensor being configured to monitor the pressure of the fluid supplied to one of the valves. As such, pressure measurements may be obtained that allow for the inflation/deflation level of each balloon valve to be individually monitored.

Moreover, as will be described below, the actuator assembly may also include a sensor communications device for wirelessly transmitting the pressure measurements provided by the pressure sensor(s) to a separate device located exterior to the patient. For example, in several embodiments, the exterior activator device may include an antenna or other suitable components for receiving wireless transmissions associated with the fluid pressure within the system. In such embodiments, the pressure measurements received from the actuator assembly may then be utilized to provide the operator of the activator device with an indication of the inflation/deflation level of the balloon valves. For instance, the activator device may include a suitable indicator means (e.g., an indicator light, a light bar, display panel and/or the like) that provides the operator an indication of when the balloon valves are fully closed/opened or a condition in which the balloons are partially inflated for the purpose of modulating flow. As such, when using the activator device to activate the actuator assembly, the operator may maintain the activator device adjacent to the location of the implanted actuator assembly (e.g., at a location adjacent to and/or contacting the patient's skin) so as to rotatably drive the driver assembly until the indicator means provides an indication that the balloons are fully inflated or fully deflated, at which point the operator may turn off the activator device or otherwise move the device away from the location of the actuator assembly. In addition to providing the operator an indication of the inflation/deflation level of the balloon valves (or as an alternative thereto), the pressure measurements may also be utilized to automatically control the operation of the activator device. For instance, in one embodiment, the activator device may be automatically turned off when it is determined that the balloon valves are fully inflated and/or fully deflated.

Additionally, in several embodiments, the sensor communications device provided within actuator assembly may be configured to be remotely powered, thereby eliminating the need for a battery to be included within the implanted assembly. For example, as will be described below, the activator device may, in one embodiment, be configured to be utilized as an initiator device for near field communications (NFC) by generating a radiofrequency (RF) field that is configured to power the sensor communications device. Thus, when the activator device is placed adjacent to the location of the implanted actuator assembly so as to magnetically drive the driver assembly, the activator device may also generate a suitable RF field for powering the sensor communication device. As a result, the sensor communications device may wirelessly transmit pressure measurements to the activator device as the activator device is being used to inflate or deflate the valve balloons, thereby providing the activator device with real-time pressure measurements that can then be used to provide a visual indication of when the valve balloons are properly inflated or deflated and/or to automatically control the operation of the activator device.

It should be appreciated that the disclosed actuator assembly and related system may generally provide numerous advantages for performing hemodialysis in patients. For example, the magnetically activated device may allow for the valves to be activated using a reusable, hand-held activation device. As such, there is no need for additional hypodermic needles that must be thrown away after use, thereby substantially reducing the ongoing costs for performing hemodialysis. In addition, the needle-free, external activation provided via the disclosed system may increase patient comfort. Moreover, the various components of the disclosed system are relatively inexpensive and easy to manufacture. Further, the ability to wirelessly monitor the pressure within the system provides an efficient and effective means for ensuring that the valves have been properly opened and/or closed during the performance of the hemodialysis process.

Referring now to FIG. 1, for purposes of explanation, a right arm 10 of a patient is shown. Selected arteries (shown as dotted pathways) are illustrated in conjunction with selected veins (shown as dark pathways). An arteriovenous graft 12 is shown connected at one end to an artery and at an opposite end to a vein. In particular, the arteriovenous graft 12 is connected to the brachial artery 14 and to the cephalic vein 16.

Figure 2:
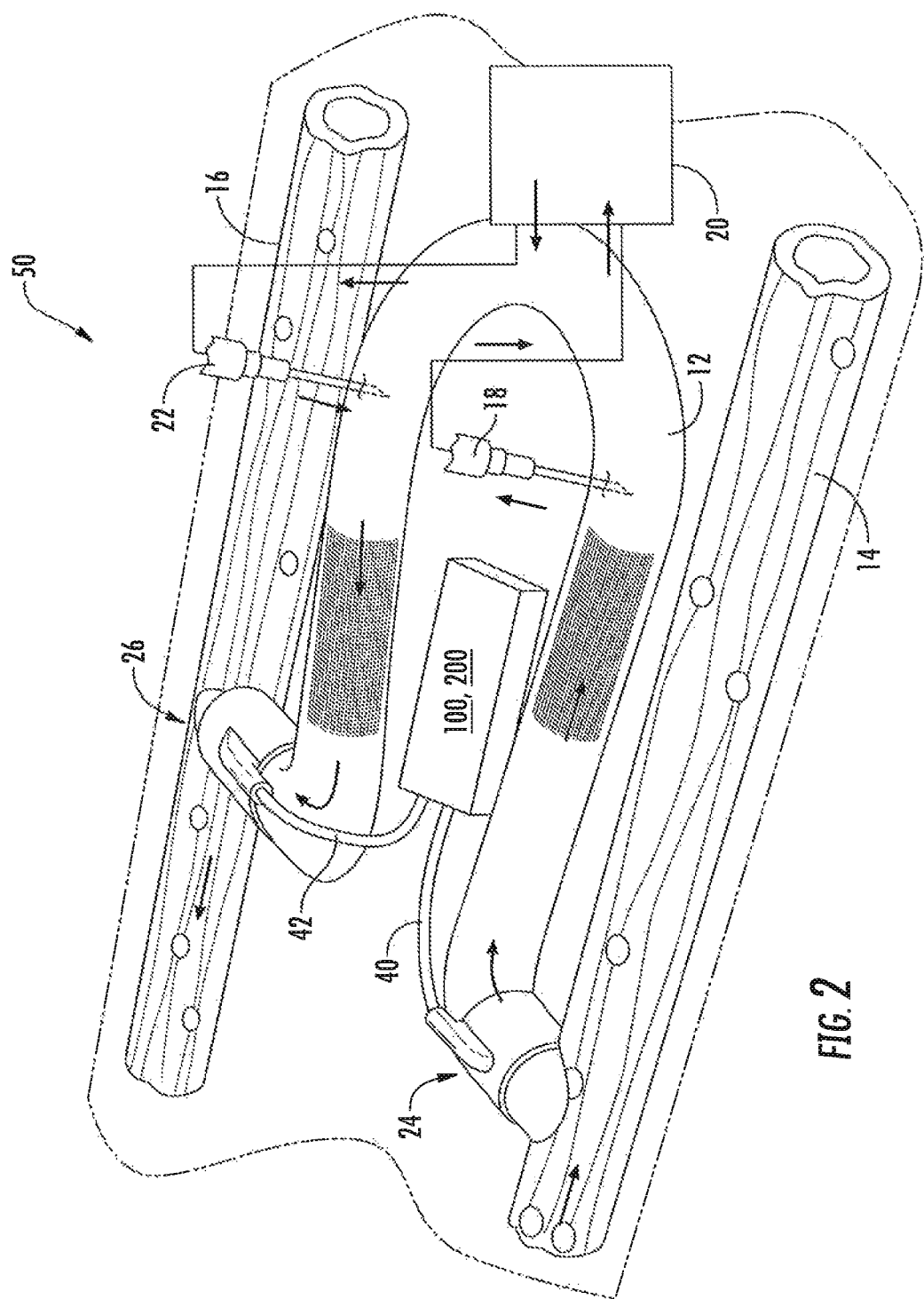
FIG. 2 illustrates a simplified, perspective view of one embodiment of arteriovenous access valve system in accordance with aspects of the present subject matter.

Referring now to FIG. 2, one embodiment of an arteriovenous access valve system 50 is illustrated in accordance with aspects of the present subject matter. As shown, the system 50 may include an arteriovenous graft 12 coupled between an artery 14 and a vein 16. In order to carry out hemodialysis, a first hypodermic needle 18 is inserted through the skin and into the arteriovenous graft 12. Blood is removed from the arteriovenous graft 12 through the needle and into a dialysis machine 20. In the dialysis machine, waste materials are removed from the blood. After circulating through the dialysis machine 20, the blood is then fed back into the arteriovenous graft 12 through a second hypodermic needle 22.

In addition, the system 50 may include a first valve device 24 (hereinafter referred to simply as the first valve 24 or valve 24) positioned at or adjacent to the arterial end of the arteriovenous graft 12 and a second valve device 26 (hereinafter referred to simply as the second valve 26 or valve 26) positioned at or adjacent to the venous end of the arteriovenous graft. In this regard, one or more components of the valves 24, 26 (e.g., a sleeve of the valves 24, 26) may have a complimentary shape to the artery and/or vein and define holes (not shown) to permit direct suturing between the device(s) and the artery and/or vein to further reinforce the connection and prevent each valve 24, 26 from moving away from its intended location. The valves 24, 26 are in an open position during normal hemodialysis as shown in FIG. 2. When hemodialysis has ended, however, the valves 24, 26 are moved to a closed position in order to prevent blood flow through the arteriovenous graft 12. In this manner, arterial steal is either eliminated or reduced. Further, by reducing turbulent blood flow through the arteriovenous graft, graft thrombosis is also prevented.

In several embodiments, the valves 24, 26 may correspond to balloon-actuated valves and, thus, may each include an inflatable balloon (not shown). When inflated, the balloons close the valves 24, 26 in a manner that reduces or eliminates the blood flow through the graft 12. In contrast, when the balloons are deflated, the valves 24, 26 are opened and blood may be directed through the arteriovenous graft 12. As will be described in greater detail below, to provide for such inflation/deflation of the balloons, the first and second valves 24, 26 may be in fluid communication with an actuator assembly 100, 200 (e.g., via tubing). Specifically, as shown in the illustrated embodiment, the actuator assembly 100, 200 may be in fluid communication with the first valve device 24 via a first valve tube 40 and may be in fluid communication with the second valve device 26 via a second valve tube 42.

Figure 3:
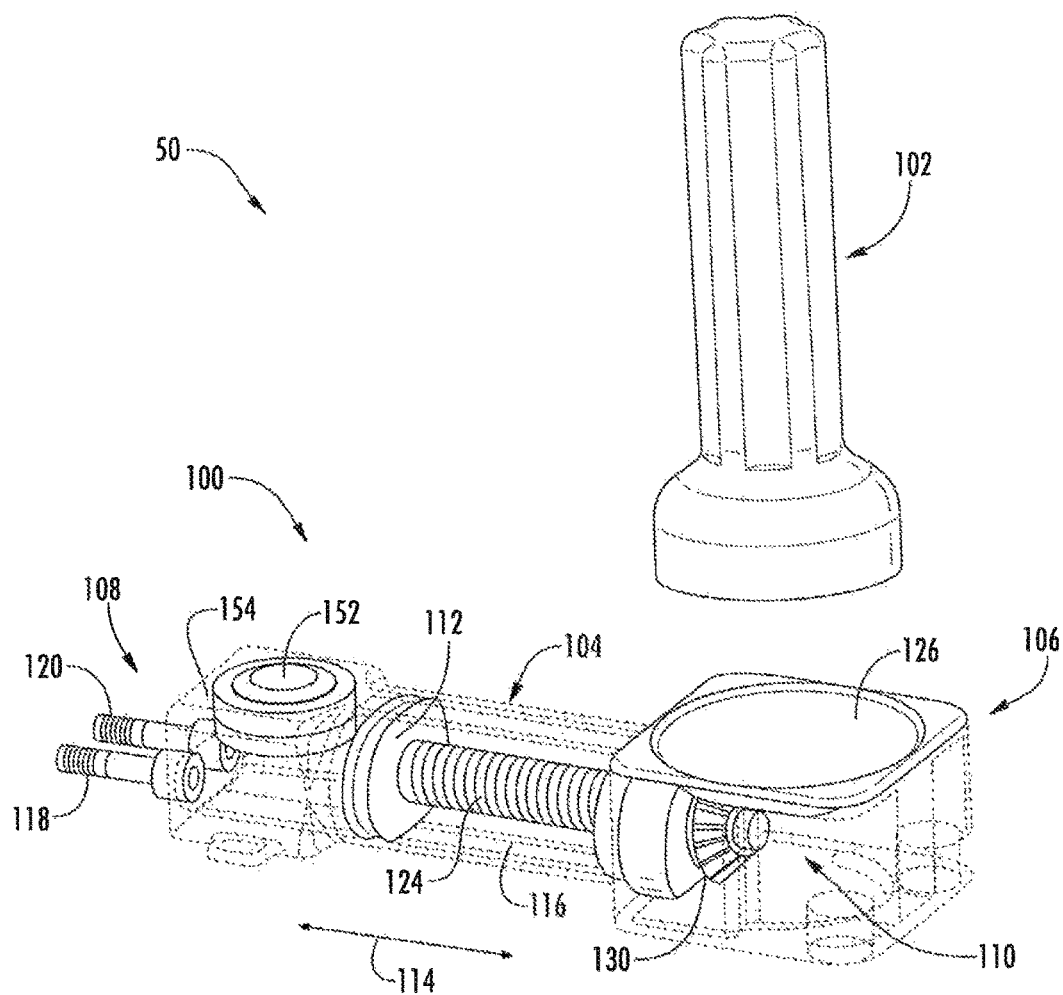
FIG. 3 illustrates a perspective view of one embodiment of an actuator assembly and a corresponding activator device that may be utilized within the disclosed system in accordance with aspects of the present subject matter, with various exterior surfaces and/or walls of the assembly being shown as see-through or transparent (e.g., via the dashed lines) to illustrate the internal components of the assembly.
Figure 4:
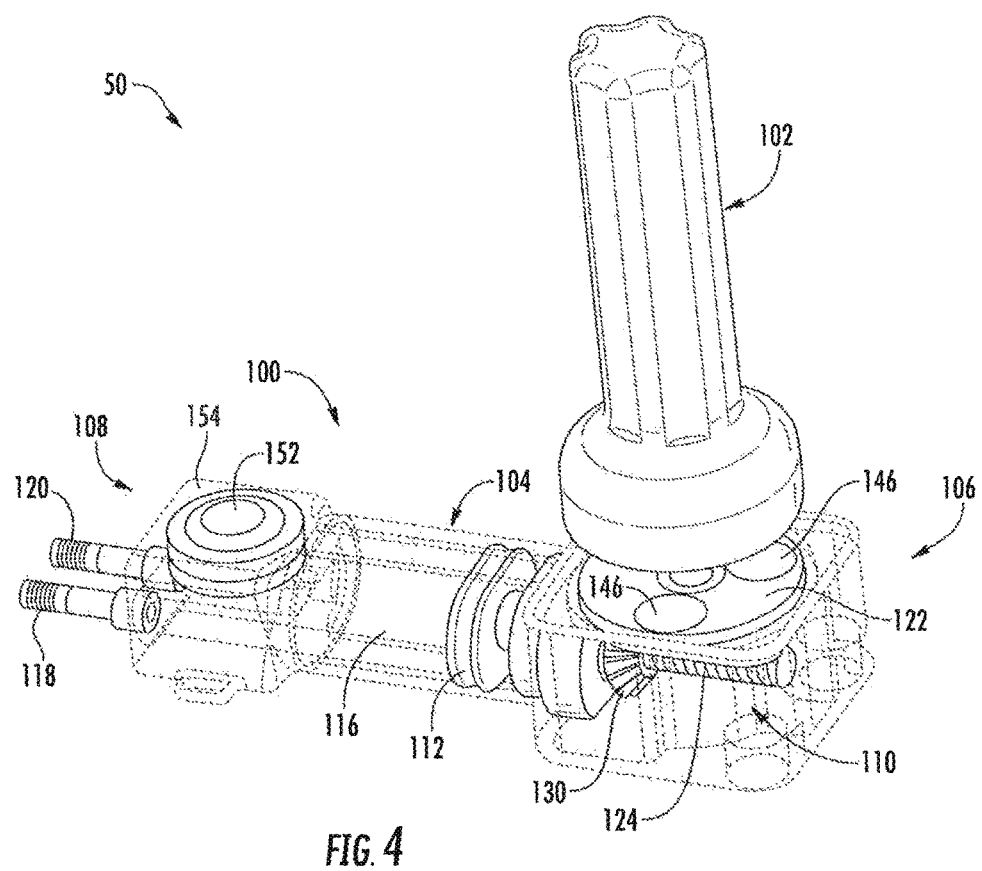
FIG. 4 illustrates another perspective view of the actuator assembly and the activator device shown in FIG. 3, particularly illustrating components of the actuator assembly in an unactuated position, with various exterior surfaces and/or walls of the assembly being shown as see-through or transparent (e.g., via the dashed lines) to illustrate the internal components of the assembly.
Figure 5:
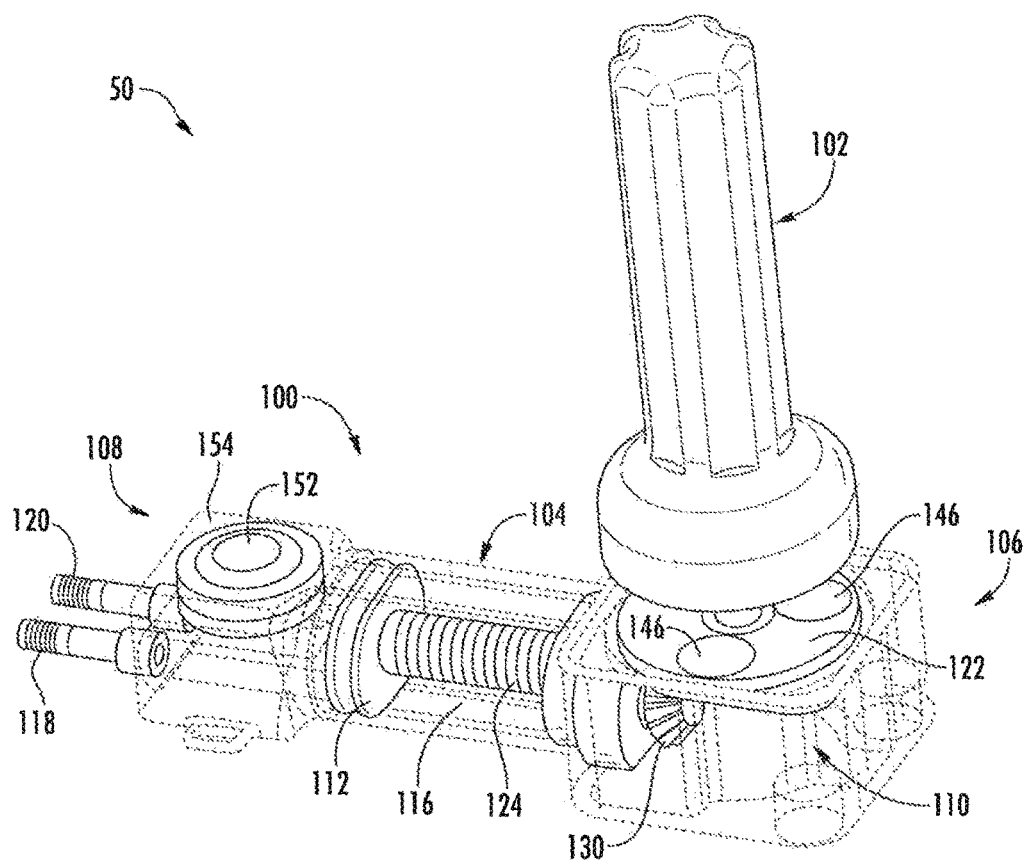
FIG. 5 illustrates a further perspective view of the actuator assembly and the activator device shown in FIG. 3, particularly illustrating components of the actuator assembly in an actuated position, with various exterior surfaces and/or walls of the assembly being shown as see-through or transparent (e.g., via the dashed lines) to illustrate the internal components of the assembly.
Figure 6:
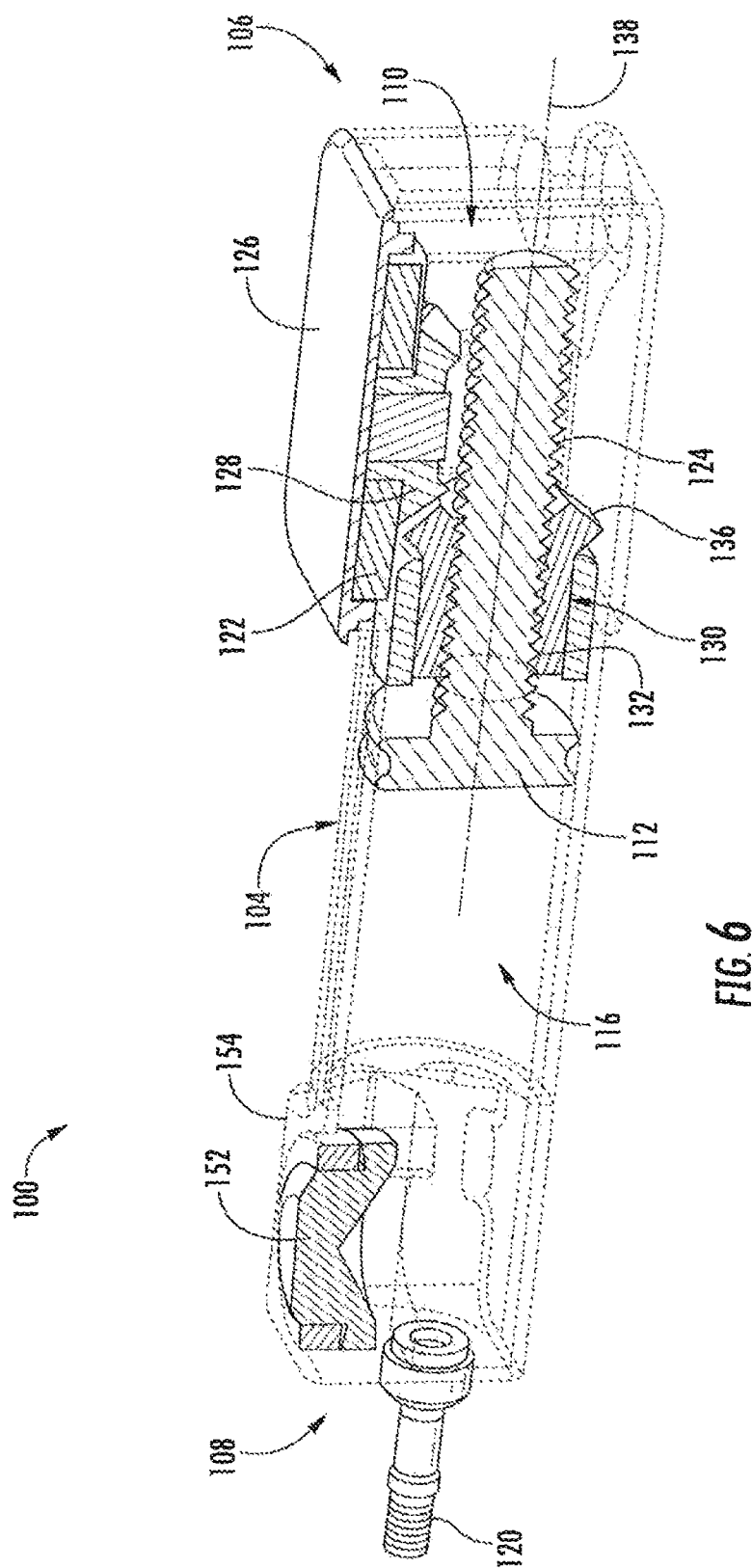
FIG. 6 illustrates a cross-sectional view of the actuator assembly shown in FIGS. 3-5.
Figure 7:
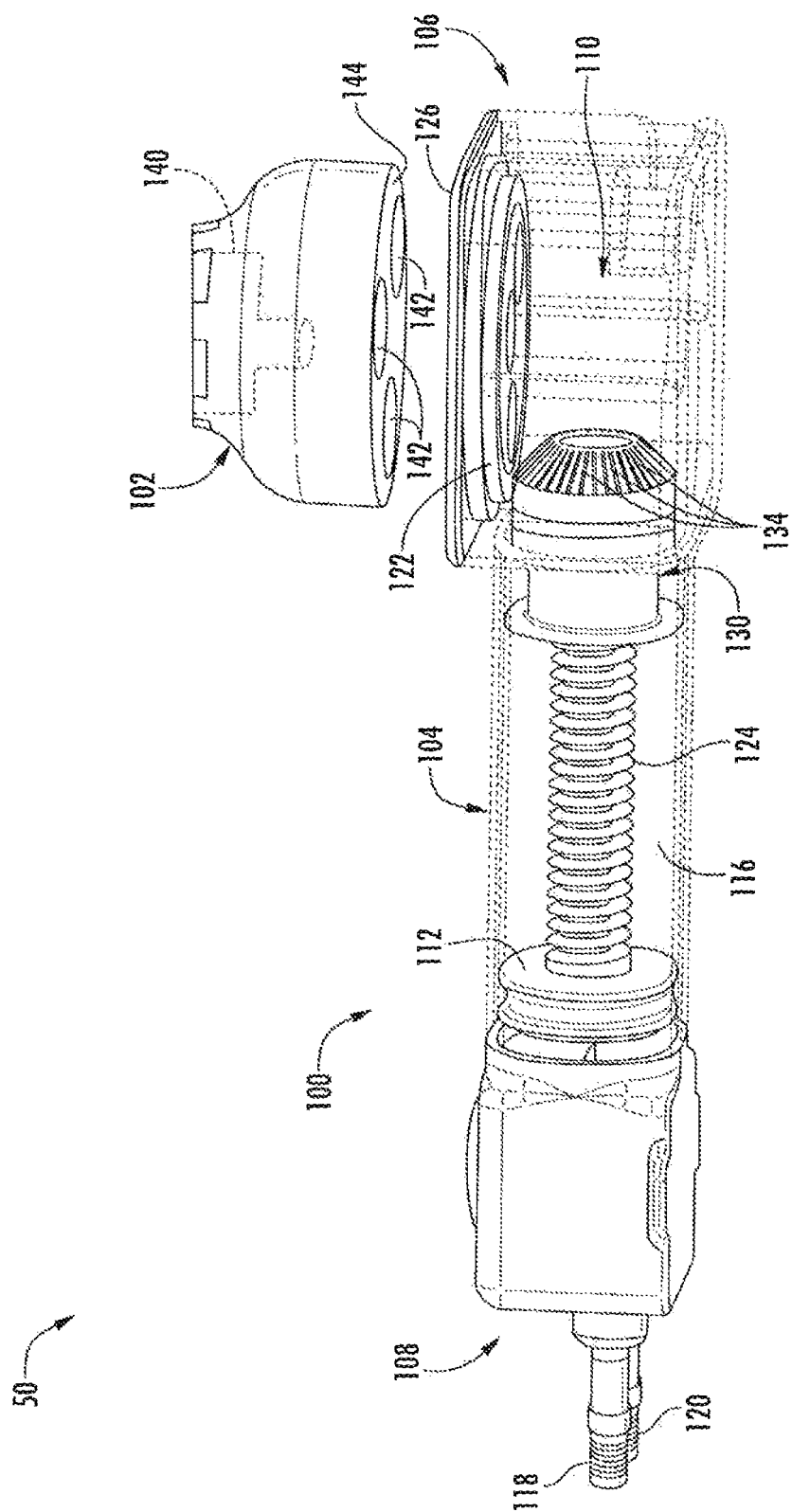
FIG. 7 illustrates a simple line drawing of the actuator assembly shown in FIGS. 3-6, particularly illustrating various exterior surfaces and/or walls of the assembly as being see-through or transparent (e.g., via the dashed lines) to illustrate the internal components of the assembly.
Figure 8:
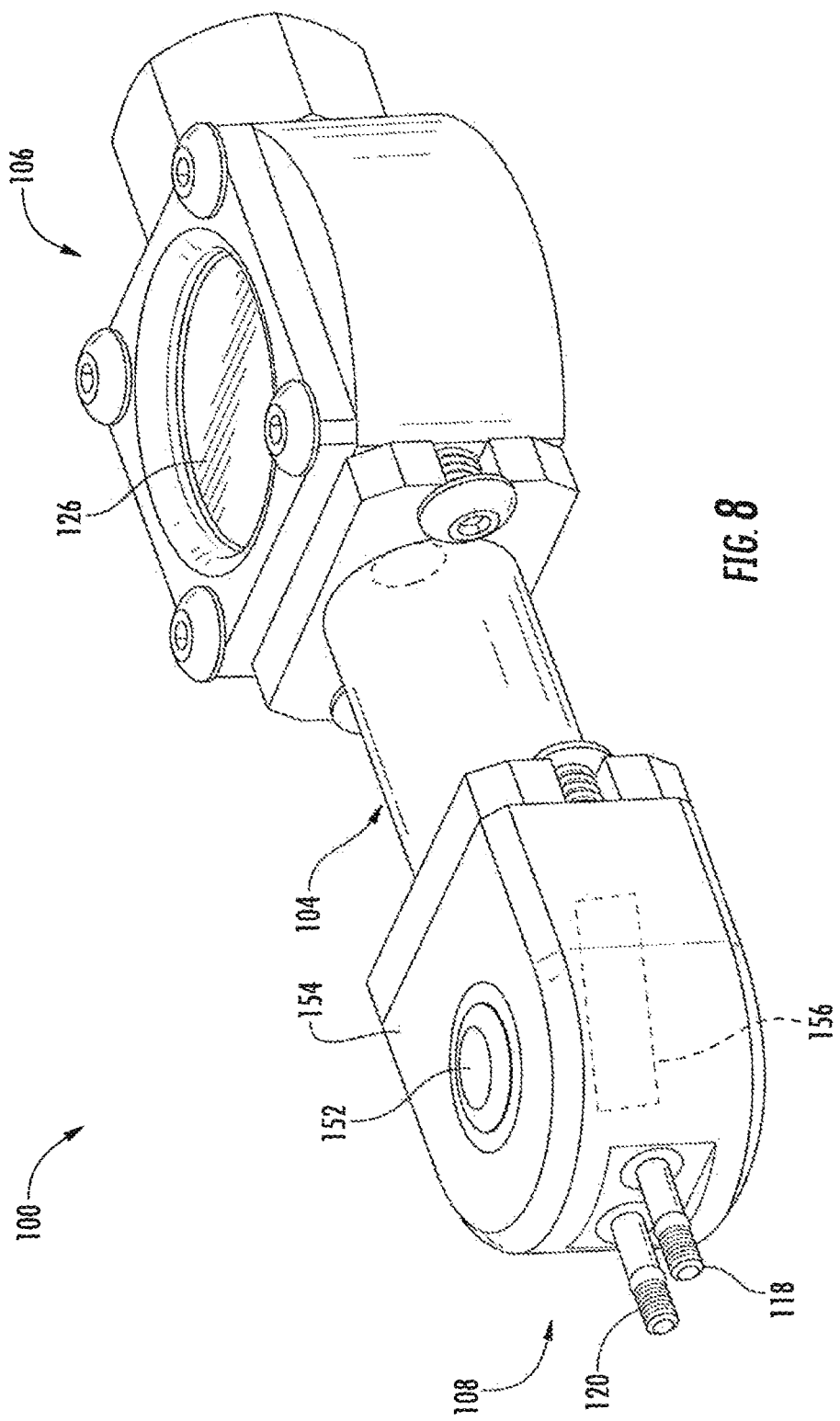
FIG. 8 illustrates yet another perspective view of the actuator assembly shown in FIGS. 3-7.
Figure 9:
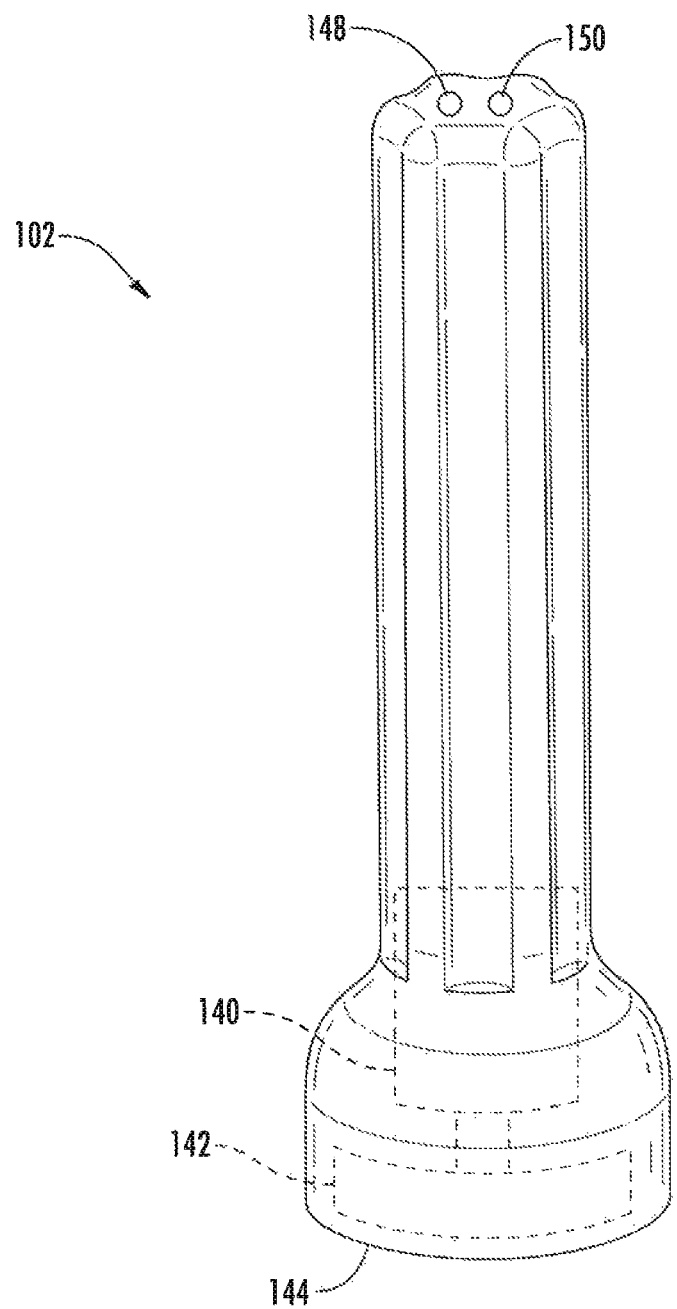
FIG. 9 illustrates a side view of the activator device shown in FIGS. 3-5.

Referring now to FIGS. 3-9, various views of one embodiment of an actuator assembly 100 suitable for use within the disclosed system 50 are illustrated in accordance with aspects of the present subject matter. Specifically, FIG. 3 illustrates a perspective view of the actuator assembly 100 and one embodiment of an associated activator device 102 that may be used in connection with the actuator assembly 100 in accordance with aspects of the present subject matter. FIGS. 4 and 5 illustrate additional perspective views of the actuator assembly 100 and the associated activator device 102, particularly illustrating components of the actuator assembly 100 in an unactuated position (FIG. 4) and an actuated position (FIG. 5). FIG. 6 illustrates a cross-sectional view of the actuator assembly 100 shown in FIGS. 3-5. FIG. 7 illustrates a line drawing of the actuator assembly 100, particularly illustrating various internal components of the actuator assembly 100 (and also including one or more internal components of the actuator assembly 100 removed for purposes of illustrating features of other internal components). FIG. 8 illustrates another perspective view of the actuator assembly 100. Additionally, FIG. 9 illustrates a side view of the activator device 102. It should be appreciated that in some or all of FIGS. 3-8, various exterior surfaces and/or walls of the actuator assembly 100 have been illustrated as fully or semi-transparent (e.g., via the dashed lines) to allow for the various internal components of the assembly 100 to be shown in the drawings for purposes of describing the present subject matter.

As shown in the illustrated embodiment, the actuator assembly 100 may generally include a housing 104 configured to serve as an outer casing or shell for the various internal components of the assembly 100. As indicated above, the actuator assembly 100 may be configured to be subcutaneously implanted within a patient, such as in the patient's arm or leg. As such, it should be appreciated that the housing 104 may generally be made from any suitable biocompatible material, such as a suitable rigid biocompatible material (e.g., titanium).

In general, the housing 104 may be configured to extend lengthwise between a first end 106 and a second end 108. As shown in the illustrated embodiment, a driver assembly 110 of the actuator assembly 100 may be associated with and/or housed within the housing 104 at or adjacent to its first end 106. As will be described below, the driver assembly 110, when activated, may be configured to drive a plunger 112 forward and backwards in the directions indicated by arrows 114 shown in FIG. 3, thereby allowing a suitable fluid (e.g., a saline solution) to be both discharged from and aspirated back into a fluid chamber 116 defined within the housing 104. Additionally, as shown in the illustrated embodiment, the actuator assembly 100 may include a first outlet port 118 and a second outlet port 120 extending from and/or defined through the second end 108 of the housing 104. As will be described below, the outlet ports 118, 120 may be in fluid communication with both the fluid chamber 116 and the valves 24, 26 (e.g., via valve tubes 40, 42). Thus, as the fluid is discharged from the fluid chamber 116 by moving the plunger 112 in the direction of the outlet ports 118, 120, the fluid may be directed through the ports 118, 120 and into the corresponding valves 24, 26 in order to close each valve 24, 26 (e.g., by inflating the associated balloons). Similarly, to open the valves 24, 26, the plunger 112 may be moved in the opposite direction to aspirate the fluid back into the fluid chamber 116.

It should be appreciated that, in several embodiments, the housing 104 may be configured to be formed from a plurality of different housing components. In such embodiments, the various housing components may be configured to be coupled together using any suitable attachment means known in the art, as mechanical fasteners, brackets, threaded components, sealing mechanisms, adhesives and/or the like and/or using any suitable attachment process known in the art, such as welding (e.g., laser welding).

In several embodiments, the driver assembly 110 may include a rotatable driver 122 configured to linearly actuate a threaded member 124 (e.g., a screw) coupled to the plunger 112. For example, as shown in the illustrated embodiment, the rotatable driver 122 may correspond to a rotatable driver disc 122 positioned within the housing 104 adjacent to an outer face 126 of the housing 104 defined at or adjacent to its first end 106. The driver disc 122 may, in turn, be coupled to the threaded member 124 via one or more intermediate driver members 128, 130 such that rotation of the disc 122 results in linear translation of the threaded member 124. For instance, as particularly shown in FIG. 6, the driver disc 122 may include a driver wheel or gear 128 formed integrally therewith or coupled thereto such that the driver gear 128 rotates with rotation of the disc 122. Additionally, as shown in FIG. 6, the driver gear 128 may, in turn, be rotatably coupled to a linear driver 130 defining a threaded opening 132 configured to receive the threaded member 124. For example, in a particular embodiment, a plurality of gear teeth 134 (FIG. 7) may be defined around an end surface 136 (FIG. 6) of the linear driver 130 that are configured to rotationally engage the corresponding gear teeth of the driver gear 128. As such, as the driver gear 128 is rotated with the rotatable disc 122, the rotational engagement between the driver gear 128 and the linear driver 130 may allow for rotation of the linear driver 130 about a longitudinal axis 138 (FIG. 6) of the threaded member 124.

Moreover, given the threaded engagement defined between the threaded opening 132 of the linear driver 130 and the threaded member 124, rotation of the linear driver 130 about the longitudinal axis 138 of the threaded member 124 may cause the threaded member 124 and, thus, the plunger 112 coupled thereto to be translated linearly within the fluid chamber 116 between an unactuated position (FIGS. 4 and 6) and an actuated position (FIGS. 3, 5 and 7). Such linear translation of the plunger 112 within the fluid chamber 116 may allow for the fluid to be discharged from and drawn back into the chamber 116 when opening and closing the valves 24, 26, respectively.

For example, referring particularly to FIG. 6, when the plunger 112 is located in the unactuated position, a significant portion of the fluid used to actuate the valves 24, 26 may be contained within the fluid chamber 116. By rotating the rotatable driver 122 in a first direction (e.g., in a clockwise direction), the plunger 112 may be moved from the unactuated position (as shown in FIG. 6) to the actuated position (e.g., as shown in FIG. 5), thereby pushing or forcing the fluid out of the fluid chamber 116. As a result, the fluid may be directed through the outlet ports 118, 120 and into the valves 24, 26 (e.g., via valve tubes 40, 42) in order to inflate the associated balloons and, thus, move the valves 24, 26 to the closed position. Thereafter, in order to open the valves 24, 26, the rotatable driver 122 may be rotated in the opposite direction (e.g., in a counter-clockwise direction), which may cause the plunger 112 to be moved from the actuated position back to the unactuated position. Such movement of the plunger 112 may generally result in the fluid being drawn back into the fluid chamber 116, thereby deflating the balloons and opening the valves 24, 26.

It should be appreciated that, given the disclosed configuration, the plunger 112 may operate similar to the plunger included within a needle or syringe. For instance, a seal may be created at the interface defined between the outer perimeter of the plunger 112 and the inner walls of the fluid chamber 116. Thus, as the plunger 112 is moved to the actuated position, it may effectively push the fluid out of the chamber 116. Similarly, a vacuum may be created within the fluid chamber 116 as the plunger 112 is retracted to the unactuated position that causes the fluid to be drawn form the balloons and back into the chamber 116.

In accordance with several aspects of the present subject matter, the driver assembly 110 may be configured to be activated or driven magnetically using the disclosed activator device 102. Specifically, in several embodiments, the rotatable driver disc 122 may be configured to be rotatably driven by one or more rotating magnets contained within the activator device 102. Thus, by placing the activator device 102 adjacent to the location of the driver assembly 110, the activator device 102 may be used to externally drive the driver assembly 110, thereby allowing the valves 24, 26 to be easily and effectively opened and closed. For instance, in one embodiment, the activator device 102 may be placed in contact with or adjacent to the patient's skin at a location directly above the location of the driver assembly 110, such as adjacent to a suitable recess formed within the housing 104 along the outer face 126 (e.g., as shown in FIGS. 3 and 8), to allow the driver assembly 110 to be magnetically driven.

In general, the activator device 102 may correspond to a small, hand-held device. As particularly shown in FIGS. 7 and 9, in several embodiments, the activator device 102 may include a reversible motor 140 rotatably coupled to one or more activator magnets 142 positioned at and/or adjacent to a contact end 144 of the device 102. The activator magnet(s) 142 may, in turn, be configured to magnetically react with all or a portion of the rotatable driver disk 122. For example, as shown in FIGS. 4 and 5, the driver disc 122 may include one or more disc magnets 146 incorporated therein and/or coupled thereto for reacting with the activator magnet(s) 142. In such an embodiment, due to the magnetic forces between the activator magnet(s) 142 and the disc magnet(s) 146, rotation of the activator magnet(s) 142 may result in rotation of the driver disc 122, thereby linearly actuating the plunger 112 and causing the fluid to be discharged from or drawn into the fluid chamber 116.

It should be appreciated that the reversible motor 140 may be configured to rotate the activator magnet(s) 142 in both a clockwise and a counter-clockwise direction. Thus, by rotating the motor 140 in a first direction, the driver disc 122 may be rotated in a direction that causes the plunger 112 to be moved to the actuated position. Similarly, by rotating the motor 140 in the opposite direction, the driver disc 122 may be rotated in the appropriate direction for moving the plunger 112 to the unactuated position. As shown in FIG. 9, in one embodiment, the activator device 102 may include suitable user control buttons 148, 150 to allow the operator to select the desired rotational direction of the motor 140. For instance, a first button 148 may be provided for rotating the motor 140 in the direction that causes the plunger 112 to be moved to the actuated position, thereby closing the valves 24, 26. Similarly, a second button 150 may be provided for rotating the motor in the opposite direction, thereby moving the plunger 112 to the unactuated position and opening the valves 24, 26.

It should be appreciated that that the activator device 102 may also include various other components and/or features. For instance, in one embodiment, activator device 102 may include all or a portion of the various components and/or features of the activator device 202 described below with reference to FIGS. 12, 20 and 21.

Referring still FIGS. 3-9, in several embodiments, the actuator assembly 100 may also include a back-up septum 152 that provide a means for adding fluid into and/or removing fluid from the actuator assembly 100 to ensure that the proper amount of fluid is contained within the assembly 100 and/or to open/close the valves 24, 26. For example, as shown in the illustrated embodiment, the septum 152 may be located on an outer face 154 of the housing 104 generally defined between the outlet ports 118, 120 and the fluid chamber 116. Thus, if necessary, a hypodermic needle may be inserted into the patient's skin and through the septum 152 to add and/or remove fluid from the actuator assembly 100. For instance, if the driver assembly 110 is not operating properly, fluid may be removed from the actuator assembly 100 via the septum 152 in order to open the valves 24, 26. Similarly, additional fluid may be added to the actuator assembly 100 via the septum 152 in order to close the valves 24, 26.

It should be appreciated that the septum 152 may be made from any suitable material capable of receiving the tip of a hypodermic needle. For example, in one embodiment, the septum 152 may be made from an elastomeric film, such as a silicone membrane.

It should also be appreciated that, in several embodiments, the actuator assembly 100 may also include a pressure accumulator 156 disposed within the housing 104. For example, as shown in FIG. 8, in one embodiment, the pressure accumulator 156 may be disposed within the housing 104 directly below the septum 152. As should be readily appreciated, the pressure accumulator 156 may be configured to assist in maintaining a constant pressure of the fluid contained within the system.

Additionally, in several embodiments, the disclosed system 50 may include a suitable means for sequentially closing the valves 24, 26. Specifically, in one embodiment, it may be desirable to close the valve positioned at the arterial end of the arteriovenous graft 12 (e.g., the first valve device 24) prior to closing the valve positioned at the venous end of the graft 12 (e.g., the second valve device 26). For example, by delaying the closing of the valve positioned at the venous end of the graft 12 by a given period of time, it may allow for any blood contained within the graft 12 to be flushed out (e.g., by injecting a blood compatible fluid into the graft 12 using, for example, a dialysis needle). Thereafter, such valve may then be closed to prevent blood from flowing back into the graft 12 from the vein.

In several embodiments, the sequential closing of the valves 24, 26 may be achieved by varying the inner diameter of the outlet ports 118, 120 of the actuator assembly 100. For instance, in a particular embodiment, the inner diameter of the outlet port in fluid communication with the valve positioned at the arterial end of the graft 12 may be larger than the inner diameter of the outlet port in fluid communication with the valve positioned at the venous end of the graft 12. As such, fluid contained within the fluid chamber 116 may be initially encouraged to flow in the direction of the valve positioned at the arterial end of the graft 12, thereby allowing such valve to be closed first. It should be appreciated that, in general, the inner diameters of the outlet ports 118, 120 may be configured to define suitable size differential that allows such valves to be sequentially closed in the manner consistent with the disclosure provided herein. For instance, in a particular embodiment, the inner diameter of the outlet port in fluid communication with the valve positioned at the venous end of the graft 12 may be smaller than the inner diameter of the outlet port in fluid communication with the valve positioned at the arterial end of the graft 12 by at least 5%, such as at least 25% or at least 50% or at least 75% or at least 90%.

In addition to varying the inner diameters of the outlet ports 118, 120 or as alternative thereto, the length and/or the inner diameter of the valve tubes 40, 42 connecting the ports 118, 120 to the valves 24, 26 may be varied in order to allow for the valves 24, 26 to be sequentially closed. For instance, the valve tube connecting the valve positioned at the venous end of the graft 12 to its corresponding outlet port may be longer than and/or define a smaller diameter than the valve tube connecting the valve positioned at the arterial end of the graft 12 to its corresponding outlet port to allow the valve positioned at the arterial end of the graft 12 to be closed first.

It should be appreciated that, in alternative embodiments, the actuator assembly 100 and/or any other related components of the system 50 may be configured such that the valves 24, 26 are simultaneously opened and closed.

It should also be appreciated that the actuator assembly 100 and/or system 50 shown in FIGS. 3-8 may additionally include various other components and/or features. For instance, in one embodiment, actuator assembly 100 and/or system 50 may include all or a portion of the various components and/or features of the actuator assembly 200 and/or system 50 described below with reference to FIGS. 12-25.

Additionally, it should be appreciated that the valves 24, 26 described herein may generally correspond to any suitable fluid-actuated valves known in the art. For example, as indicated above, in several embodiments, the valves 24, 26 may correspond to fluid-actuated balloon valves. In such embodiments, the balloon valves may generally have any suitable configuration known in the art for closing and opening the valves 24, 26 by inflating and deflating the balloons, respectively, using any suitable fluid. For instance, one embodiment, each balloon may be annular-shaped and may be configured to wrap circumferentially around the graft 12 such that, when inflated, the balloons extend radially inwardly and prevent blood from flowing through the graft. Such balloons are described, for example, in U.S. Pat. No. 7,025,741, which is hereby incorporated by reference herein in its entirety for all purposes.

Figure 10:
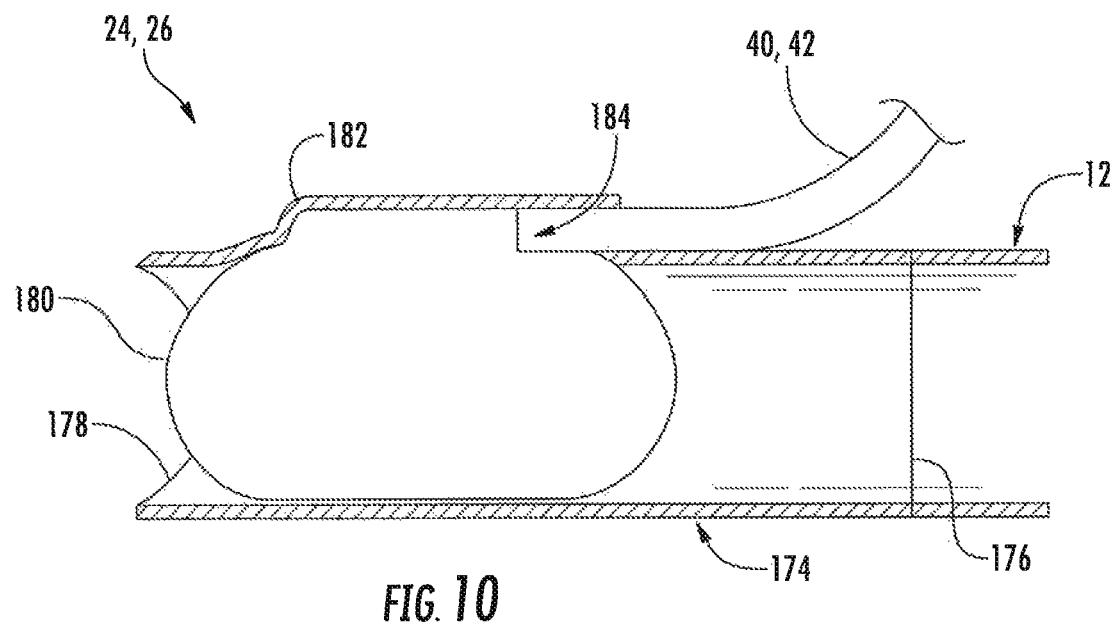
FIG. 10 illustrates a cross-sectional view of one embodiment of a fluid-actuated balloon valve suitable for use within the disclosed system, particularly illustrated the valve in a closed position.
Figure 11:
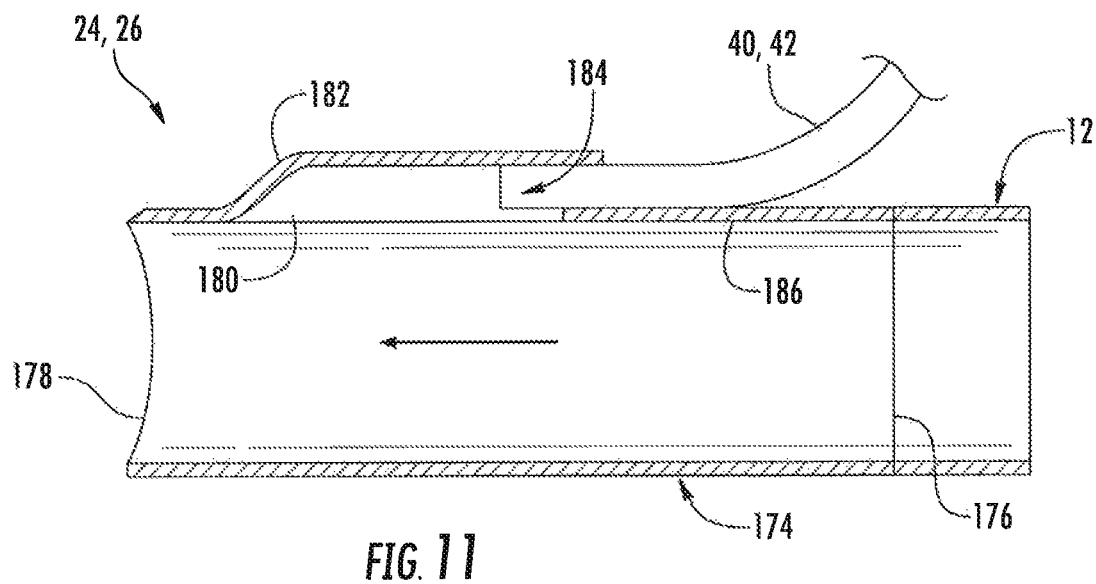
FIG. 11 illustrates another cross-sectional view of the fluid-actuated balloon valve shown in FIG. 10, particularly illustrated the valve in an open position.

In another embodiment, the balloons may be configured to be disposed in-line with the graft 12 (or in-line with any suitable coupling in fluid communication with the graft 12, such as one or more sleeves positioned within the graft 12 or coupled to the graft 12 at its ends). For instance, FIGS. 10 and 11 illustrate one example of a suitable in-line balloon valve 24, 26 that may be utilized within the disclosed system 50 in accordance with aspects of the present subject matter. Specifically, FIG. 10 illustrates the valve 24, 26 in a closed position and FIG. 11 illustrates the valve 24, 26 in an opened position.

As shown, the valve 24, 26 may include a cylindrical housing or sleeve 174 extending between a first end 176 and a second end 178, with the first end 176 of the sleeve 174 being configured to be coupled to a corresponding end of the arteriovenous graft 12 (e.g., the arterial end or the venous end of the graft 12) using any suitable attachment means (e.g., sutures (not shown)) and the second end 178 of the sleeve 174 being configured to be coupled to either an artery 14 or a vein 16 of the patient using any suitable attachment means (e.g., sutures). Alternatively, the sleeve 174 may be configured as an integral portion of the graft 12 such that the second end 178 of the sleeve 172 corresponds to the arterial or venous end of the graft 12.

Additionally, the valve 24, 26 includes a balloon 180 configured to be positioned at least partially in-line with the sleeve 174. For example, in several embodiments, the sleeve 174 may include a raised portion 182 configured to extend radially outwardly relative to the remainder of the sleeve 174 such that a recess 184 is defined directly below the raised portion 182 for receiving both the balloon 180 and the tubing 40, 42 extending between the balloon 180 and the actuator assembly 100. As such, when the balloon 180 is deflated (as shown in FIG. 11), the balloon 180 may be retracted back into the recess 184 so that the balloon provides no or minimal restriction to the flow of blood through the graft/sleeve 12, 174. For example, as shown in FIG. 11, in one embodiment, the balloon 180 may be configured to be retracted back into the recess 184 such that the inner surface of the balloon 180 is generally aligned within an inner surface 186 of the sleeve 174 and/or the graft 12. Additionally, as shown in FIG. 10, when fluid is supplied to the balloon 180 so as to close the valve 24, 26, the balloon may be configured to expand outwardly from the recess 184 into the interior of the sleeve 174 such that the balloon 180 completely blocks the flow of blood through the sleeve 174.

Figure 12:
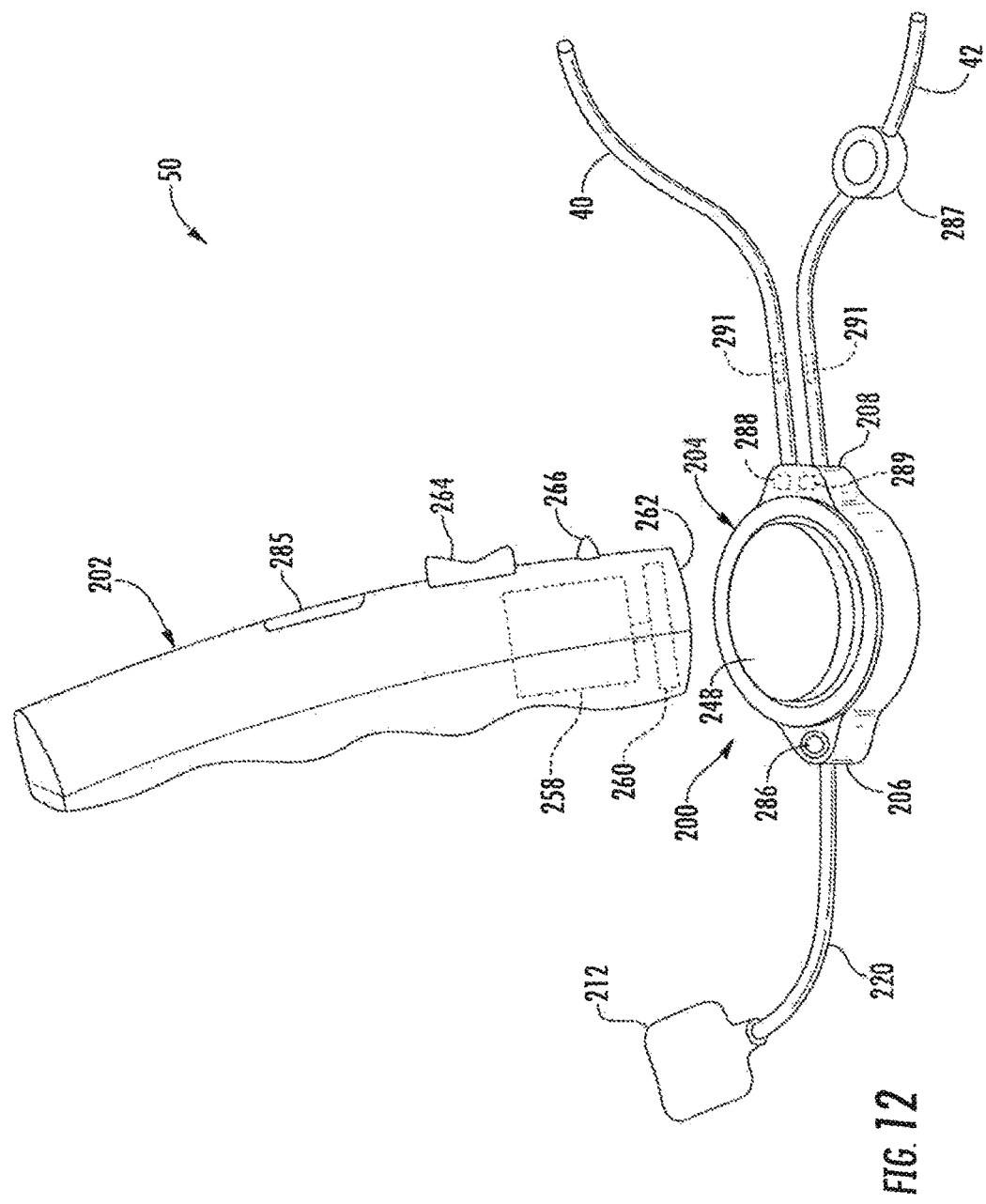
FIG. 12 illustrates a perspective view of one embodiment of an actuator assembly and a corresponding activator device (as well as various other system components) that may be utilized within the disclosed system in accordance with aspects of the present subject matter.
Figure 13:
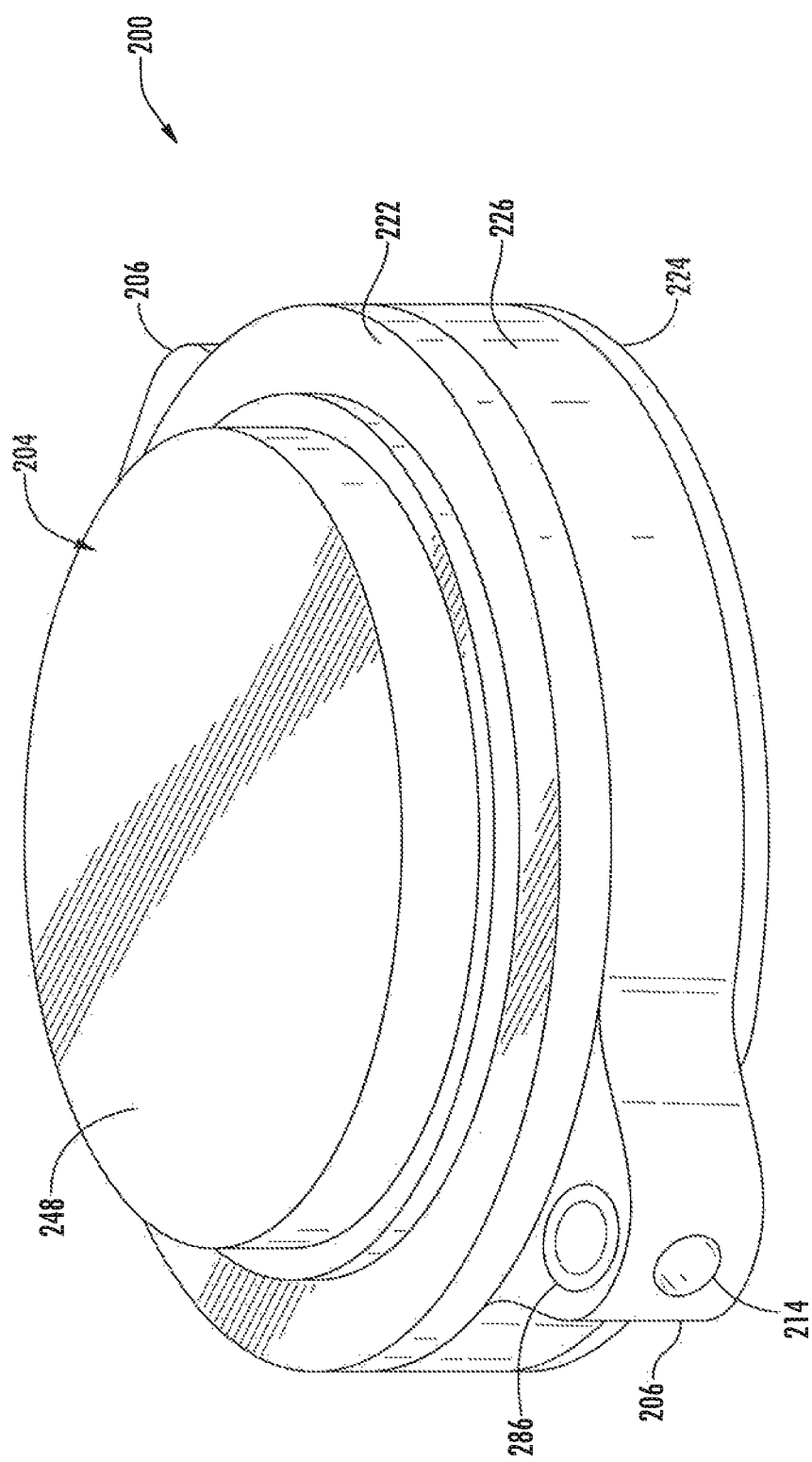
FIG. 13 illustrates a perspective view of the actuator assembly shown in FIG. 12, particularly illustrating one end of the actuator assembly.
Figure 14:
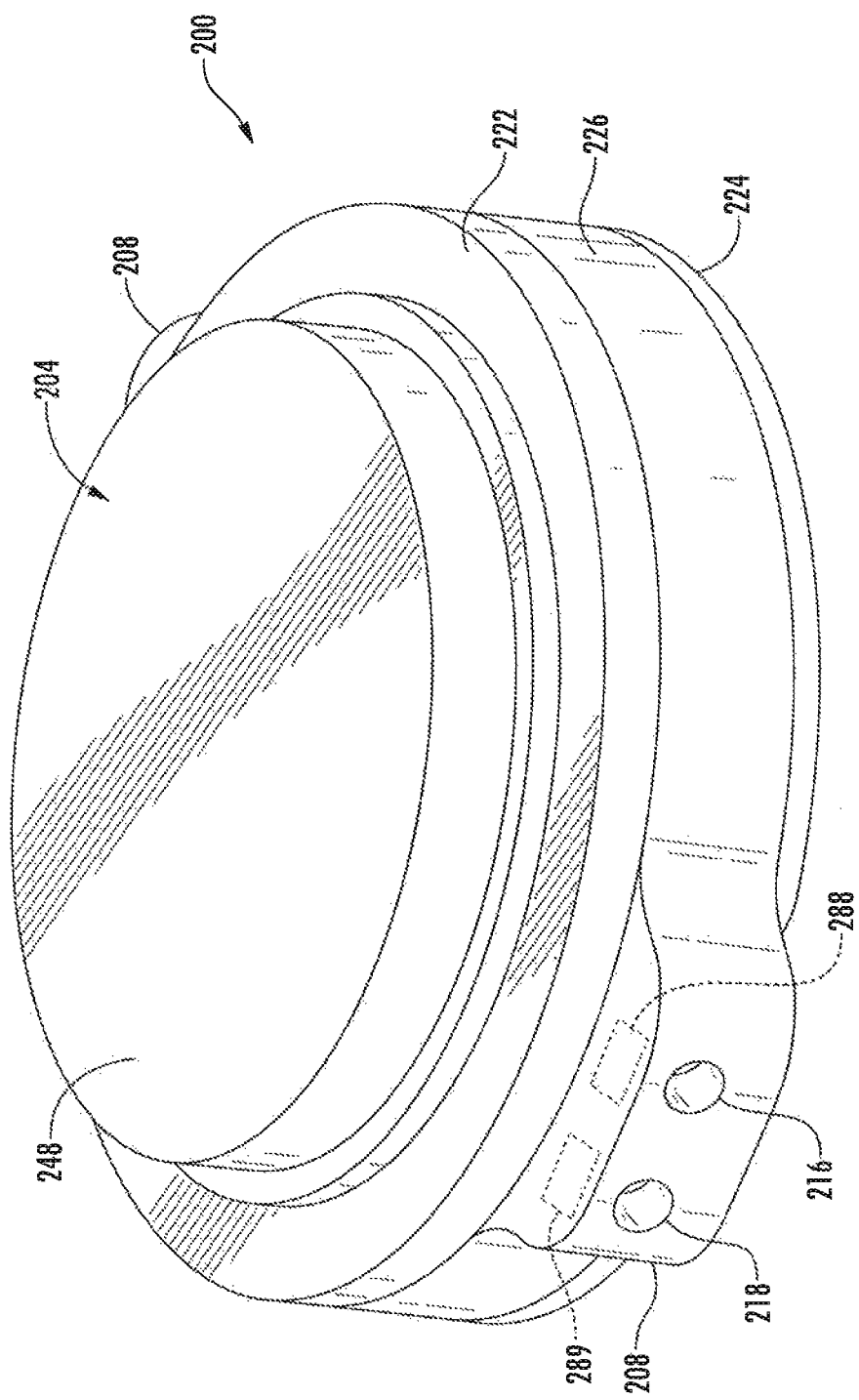
FIG. 14 illustrates another perspective view of the actuator assembly shown in FIG. 12, particularly illustrating the opposite end of the actuator assembly shown in FIG. 13.
Figure 15:
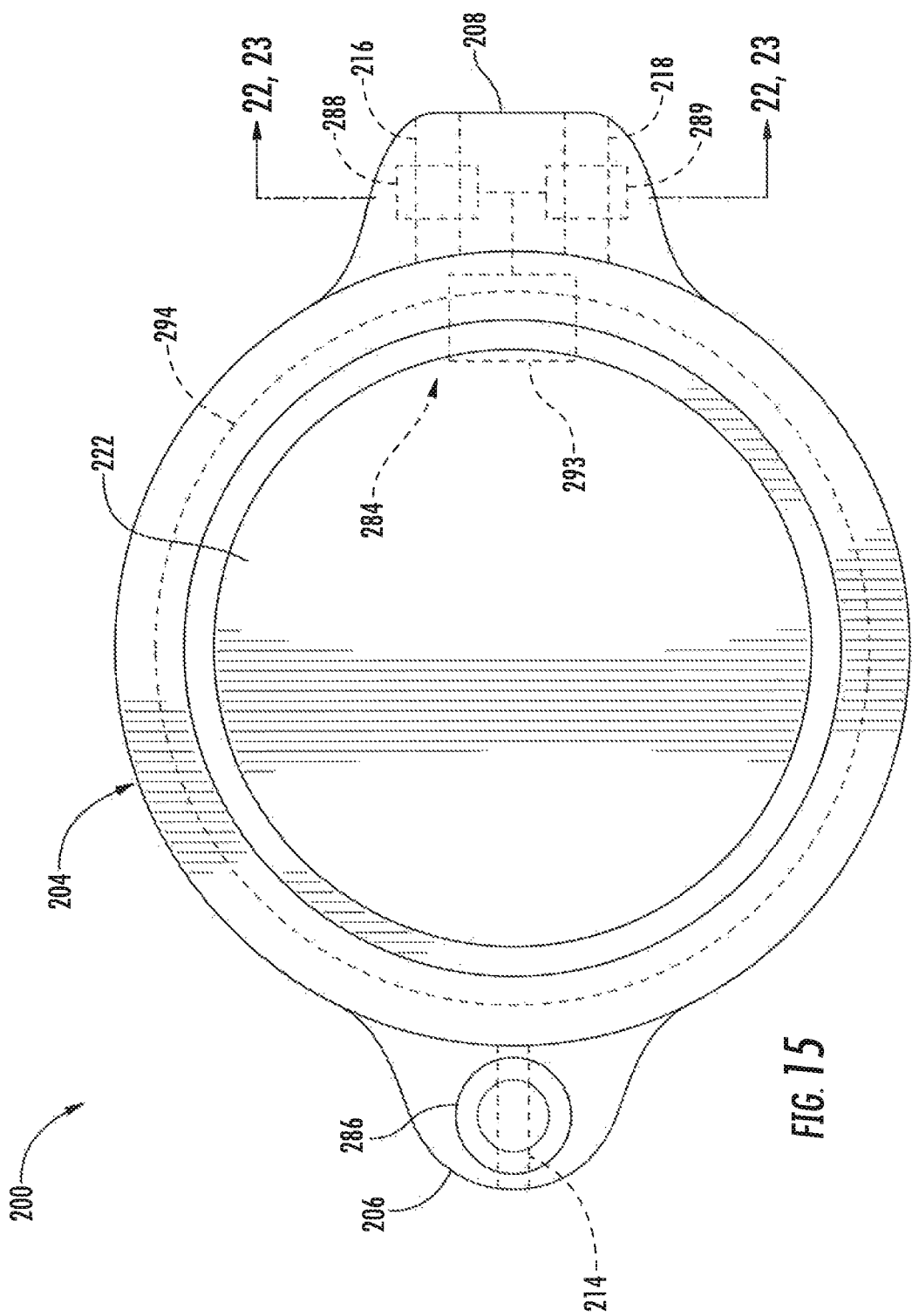
FIG. 15 illustrates a top view of the actuator assembly shown in FIG. 12, particularly illustrating various internal components and/or features of the actuator assembly in dashed or hidden lines.
Figure 16:
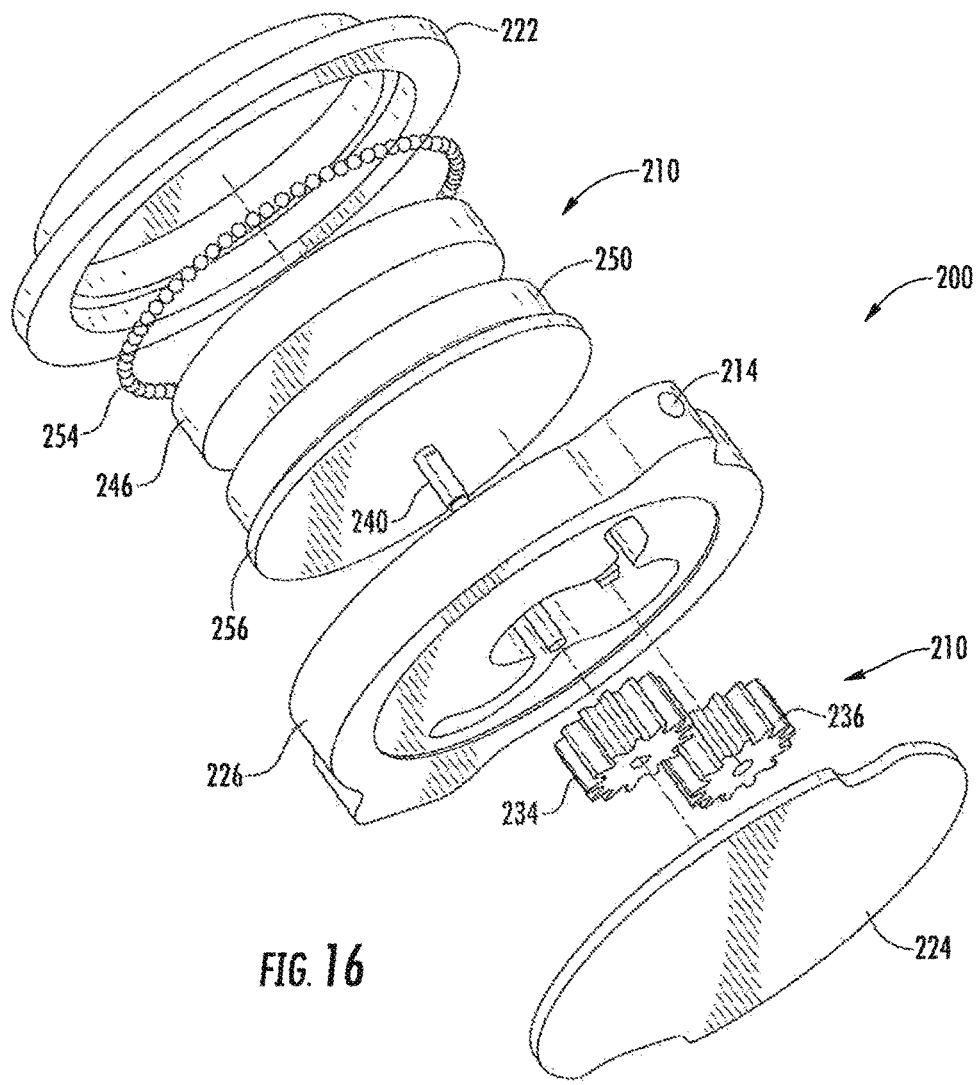
FIG. 16 illustrates an exploded view of the actuator assembly shown in FIG. 12.
Figure 17:
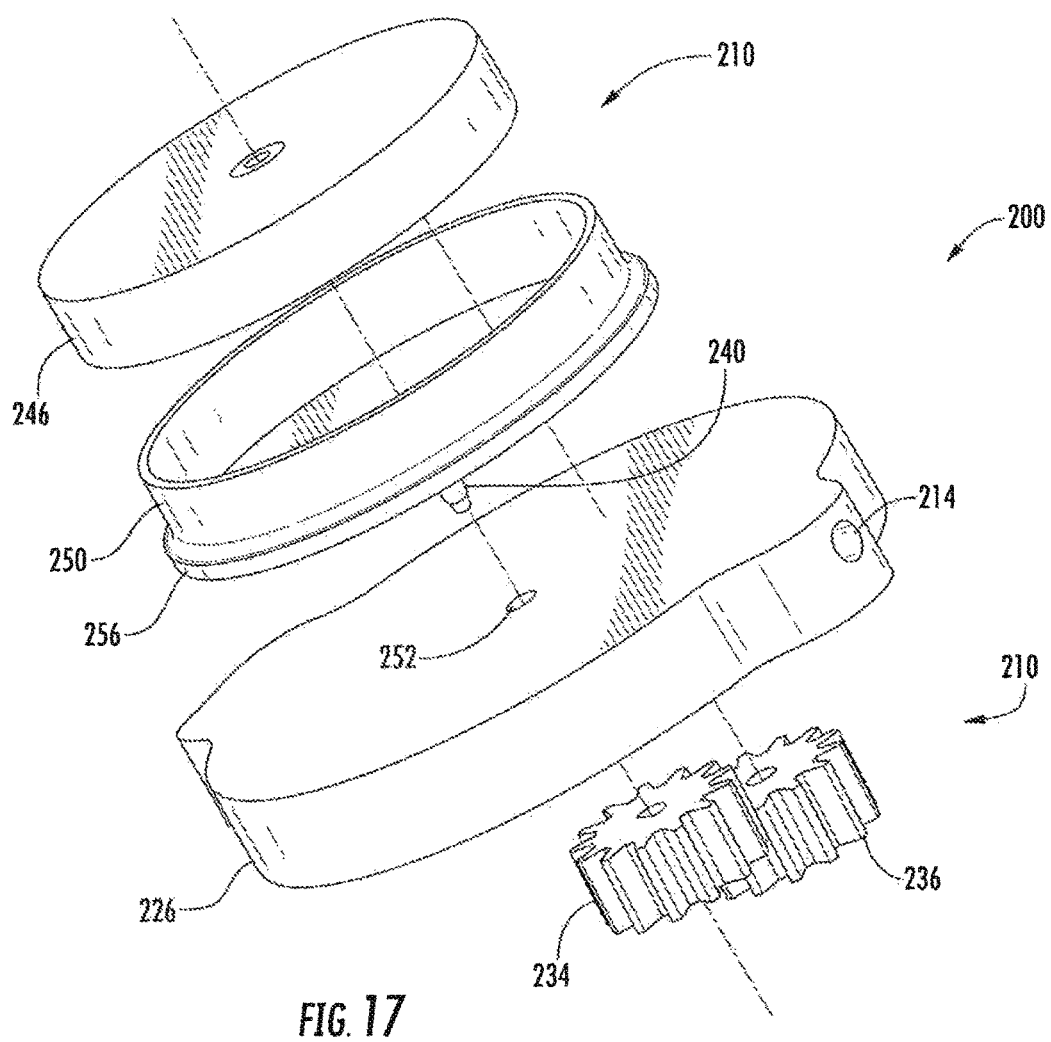
FIG. 17 illustrates another exploded view of several of the components of the actuator assembly shown in FIG. 16.
Figure 18:
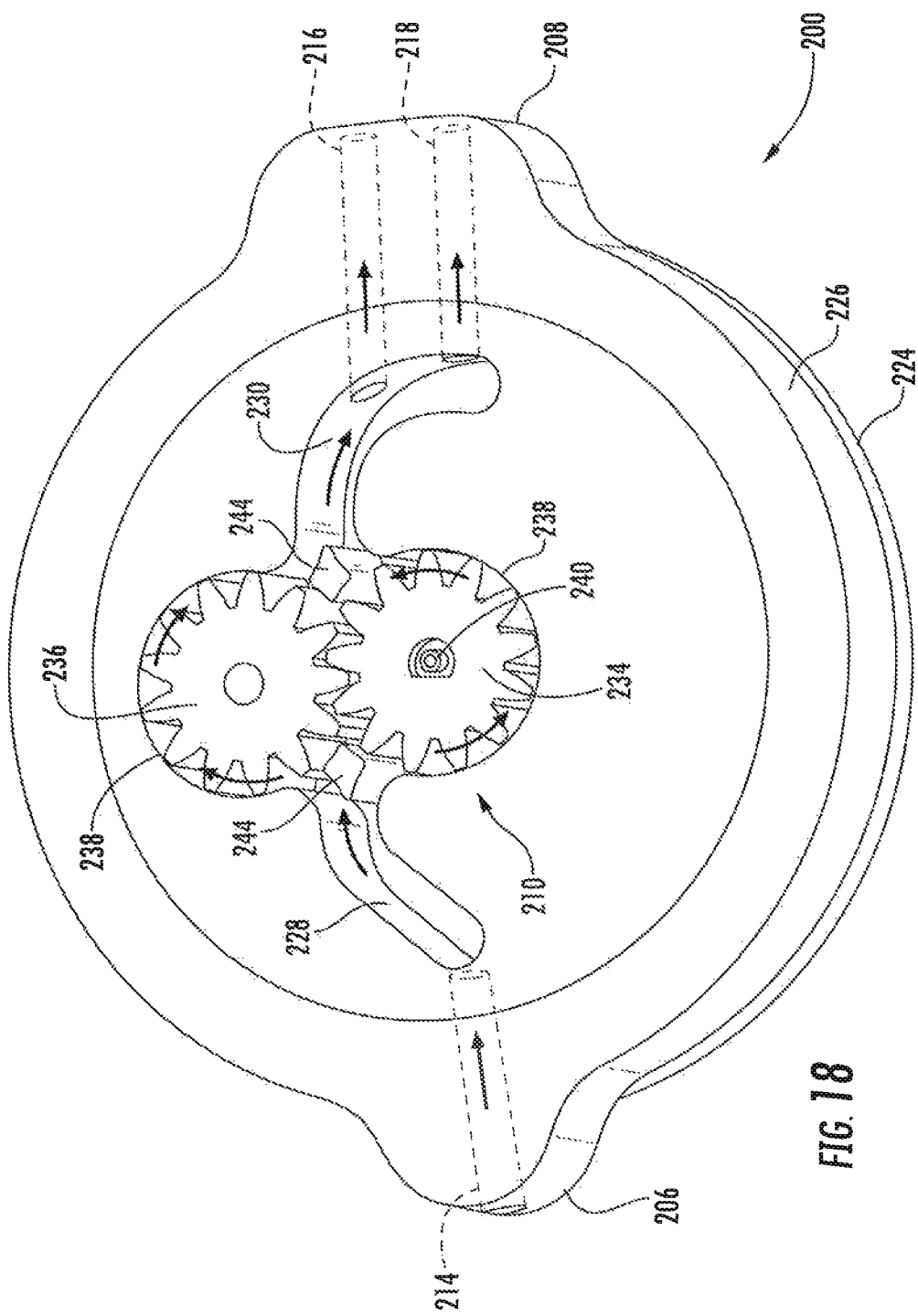
FIG. 18 illustrates a bottom perspective view of a housing component of the actuator assembly shown in FIG. 12, particularly illustrating various ports and channels defined in the housing component as well as various components of a driver assembly of the actuator assembly positioned within the housing component.
Figure 19:
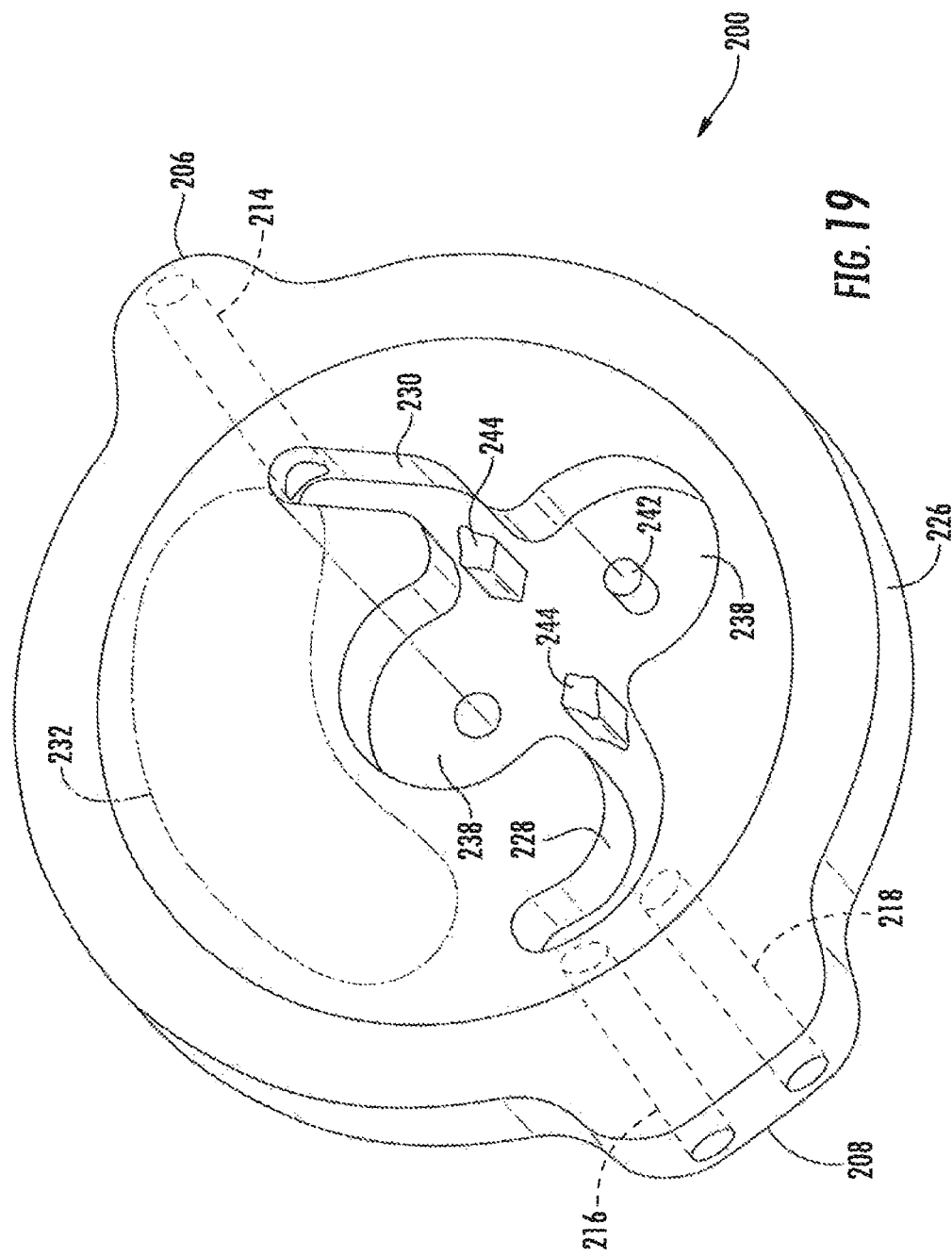
FIG. 19 illustrates another bottom perspective view of the housing component shown in FIG. 18, particularly illustrating the driver assembly components removed for purposes of illustration.
Figure 20:
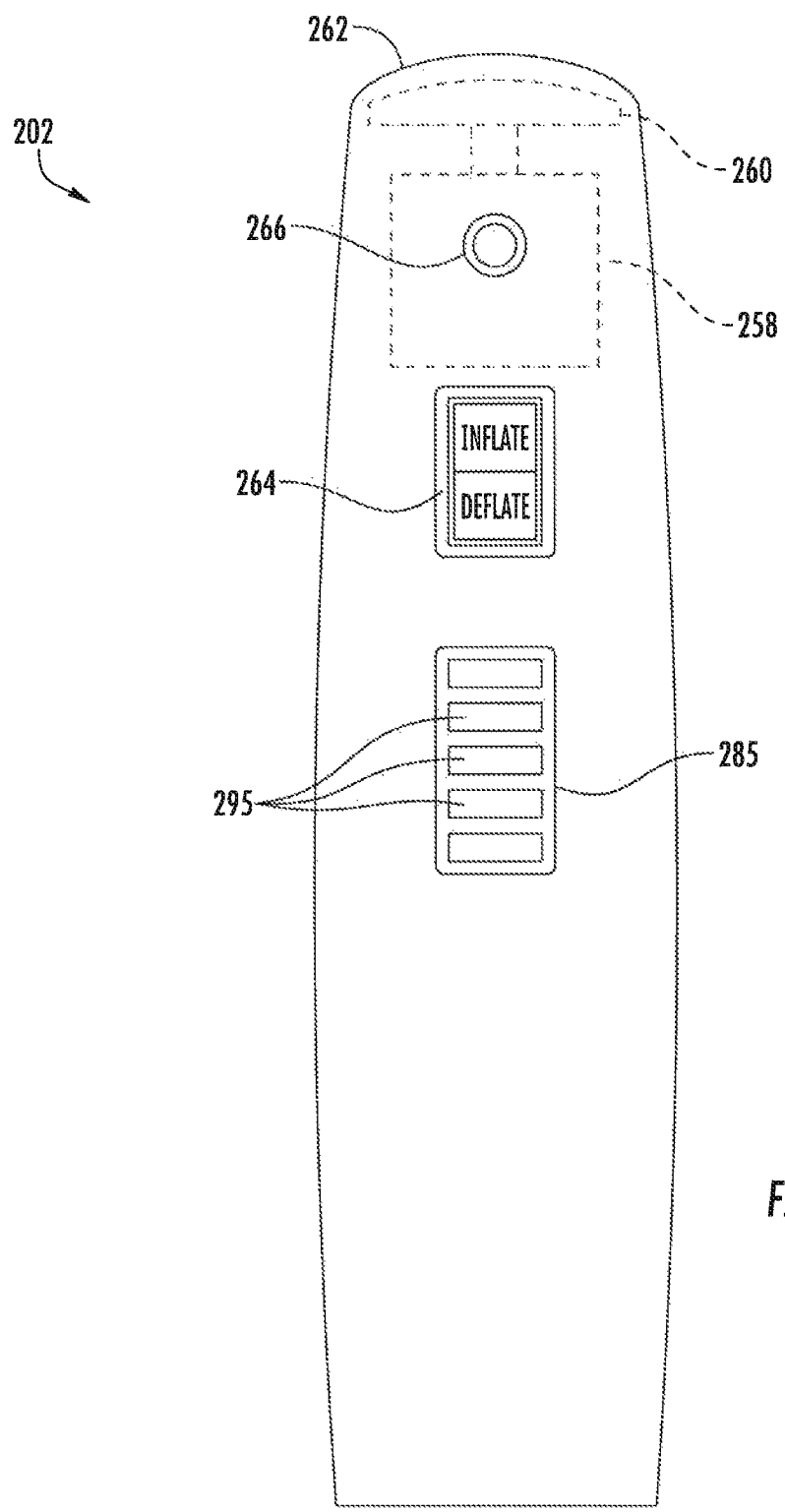
FIG. 20 illustrates a side view of the activator device shown in FIG. 12.
Figure 21:
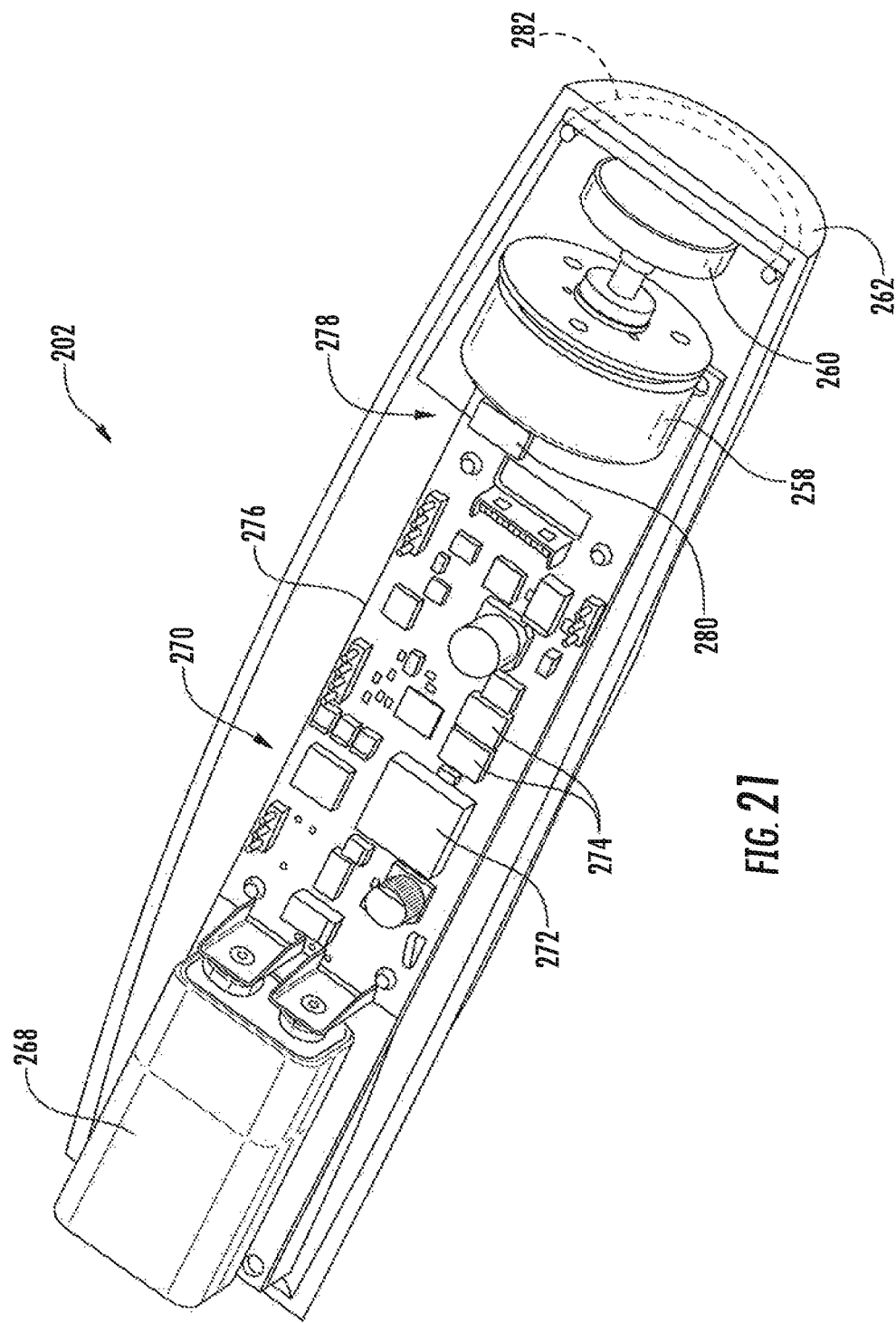
FIG. 21 illustrates a perspective view of activator device shown in FIG. 12 with a portion of an outer cover of the activator device removed to allow the various internal components of the activator device to be shown.

Referring now to FIGS. 12-21, various views of another embodiment of an actuator assembly 200 suitable for use within the disclosed system 50 are illustrated in accordance with aspects of the present subject matter. Specifically, FIG. 12 illustrates a perspective view of the actuator assembly 200 and one embodiment of an associated activator device 202 that may be used in connection with the actuator assembly 200 in accordance with aspects of the present subject matter. In addition, FIG. 12 also illustrates various other system components that may be utilized in connection with the actuator assembly 200 in accordance with aspects of the present subject matter. FIGS. 13 and 14 illustrate perspective views of opposed first and second ends, respectively, of the actuator assembly 200 shown in FIG. 12 (with the tubing shown in FIG. 12 being removed) and FIG. 15 illustrates a top view of the actuator assembly 200 shown in FIGS. 13 and 14. FIG. 16 illustrates an exploded view of the actuator assembly 200 shown in FIGS. 13-15 and FIG. 17 illustrates an exploded view of various components of the actuator assembly 200 shown in FIG. 16. FIGS. 18 and 19 illustrate differing perspective, bottom views of a housing component of the actuator assembly 200, with FIG. 18 illustrating the housing component with suitable gears installed therein and FIG. 19 illustrating the housing component with the gears removed. Additionally, FIG. 20 illustrates a front view of the activator device 202 shown in FIG. 12 and FIG. 21 illustrates a perspective view of the activator device 202 shown in FIG. 20 with at least a portion of an outer casing or shell of the device 202 being removed so as to illustrate various internal components of the activator device 202.

As shown in the illustrated embodiment, the actuator assembly 200 may generally include a housing 204 configured to serve as an outer casing or shell for the various internal components of the assembly 200. As indicated above, the actuator assembly 200 may be configured to be subcutaneously implanted within a patient, such as in the patient's arm or leg. As such, it should be appreciated that the housing 204 may generally be made from any suitable biocompatible material, such as a suitable rigid biocompatible material (e.g., titanium).

In general, the housing 204 may be configured to extend lengthwise between a first end 206 and a second end 208. As shown in the illustrated embodiment (e.g., in FIGS. 16 and 17), a magnetically-activated driver assembly 210 of the actuator assembly 200 may be associated with and/or housed within the housing 204 between its first and second ends 206, 208. As will be described below, the driver assembly 210, when activated, may be configured to pump or transport a suitable fluid (e.g., a saline solution) between a fluid chamber or reservoir 212 positioned exterior to the housing 204 and the valves 24, 26 fluidly connected to the actuator assembly 200 via the valve tubes 40, 42. Additionally, as shown in the illustrated embodiment, the actuator assembly 200 may include an inlet port 214 defined by and/or through a portion of the housing 204 (e.g., at the first end 206 of the housing 204) and first and second outlet ports 216, 218 defined by and/or through a different portion of the housing 204 (e.g., at the second end 208 of the housing 204). As will be described below, the inlet port 214 may be in fluid communication with the fluid reservoir 212 (e.g., via a suitable reservoir tube 220). Similarly, the first and second outlet ports 216, 218 may be in fluid communication with the first and second valves 24, 26, respectively (e.g., via the valve tubes 40, 42). Thus, as fluid is pumped from the fluid reservoir 212 into the housing 204 due to activation of the driver assembly 210, the fluid may be expelled from the housing 204 via the outlet ports 216, 218 and into the corresponding valves 24, 26 in order to close each valve 24, 26 (e.g., by inflating the associated balloons). Similarly, to open the valves 24, 26, the driver assembly 210 may be rotatably driven in the opposite direction to draw the fluid out of the balloons and direct it back through the housing 204 and into the fluid reservoir 212.

It should be appreciated that, in several embodiments, the housing 204 may be configured to be formed from a plurality of different housing components. For example, as shown in FIGS. 13, 14 and 16, the housing 204 may be formed from an upper housing component 222, a lower housing component 224 and a central housing component 226. In such embodiments, the various housing components 222, 224, 226 may be configured to be coupled together using any suitable attachment means known in the art, such as mechanical fasteners, brackets, threaded components, sealing mechanisms, adhesives and/or the like, and/or using any suitable attachment process known in the art, such as welding (e.g., laser welding).

In several embodiments, the central housing component 226 may be configured to define a flow path for the fluid being directed through the housing 204 between the inlet port 214 and the outlet ports 216, 218. For example, as shown in FIGS. 18 and 19, the central housing component may define an inlet flow channel 228 extending between the inlet port 214 and a gear pump of the drive assembly 210 (described below) and an outlet flow channel 230 extending between the gear pump and the outlet ports 216, 218. As such, when fluid is being directed through the housing 204 from the fluid reservoir 212 to the valves 24, 26, the fluid entering the housing 204 via the inlet port 214 may be directed into inlet flow channel 228 and through the gear pump. Thereafter, the fluid may flow through the outlet flow channel 230 and may then be expelled from the housing 204 via the outlet ports 216, 218.

Additionally, as shown in FIG. 12, the fluid reservoir 212 may generally correspond to a separate component configured to be fluidly coupled to the actuator assembly 200 via the reservoir tube 220. By providing such a separate fluid reservoir 212, the overall size of the actuator assembly 200 may be reduced significantly as compared to a configuration in which the fluid needed to actuate the valve devices 24, 26 is stored entirely within the actuator assembly 200. It should be appreciated that the fluid reservoir 212 may generally be formed from a pliable or flexible polymer material so as to allow the reservoir 212 to be positioned adjacent to the implant location of the actuator assembly 200 with minimal or no added discomfort to the patient.

It should also be appreciated that, in alternative embodiments, the actuator assembly 200 may, instead, include a fluid reservoir or chamber defined within the housing 200. Specifically, similar to the fluid chamber 116 described above with reference to FIGS. 3-9, an internal cavity may be defined within the housing 204 for containing the fluid to be supplied to the valves 24, 26. For instance, as shown in dashed lines in FIG. 19, the central housing component 226 may define an internal cavity 232 for storing fluid therein. In such instance, the system 50 need not include the separate reservoir 212 and the actuator assembly 200 need not include the inlet port 214 since fluid may be supplied directly from the internal cavity 232 to the valves 24, 26.

As particularly shown in FIGS. 16-18, in several embodiments, the driver assembly 210 may include two separate gears 234, 236 (e.g., spur gears) configured to function as a gear pump for pumping fluid between the fluid reservoir 212 and the valves 24, 26. Specifically, as shown in the illustrated embodiment, the driver assembly 210 includes a drive gear 234 and an idler gear 236, with each gear 234, 236 being configured to be positioned within a corresponding gear cavity 238 (FIGS. 18 and 19) defined by the central housing component 226. The drive gear 234 may be configured to be rotatably coupled to a corresponding drive shaft 240 of the driver assembly 210. Additionally, the idler gear 236 may be configured to be rotatably supported within its gear cavity 238 via a gear post 242 (FIG. 19) extending into the cavity 238 from the central housing component 226. In general, the gears 234, 236 may be configured to mesh with or engage one another such that, as the drive gear 234 is rotated via rotation of the drive shaft 238, the idler gear 236 may be rotated about the gear post 242. Such meshing or engagement of the gears 234, 236 may generally result in the positive displacement of fluid through the gear pump. Thus, by rotating the gears 234, 236 in a first direction, the gear pump may be configured to pump fluid from the reservoir 212 in the direction of the valves 24, 26. Similarly, by rotating the gears 234, 236 in the opposite direction, the gear pump may be configured to pump fluid from the valves 24, 26 back in the direction of the fluid reservoir 212.

An example flow path for the fluid being pumped through the housing 204 between the inlet port 214 and the outlet ports 216, 218 is illustrated by the arrows provided in FIG. 18. As shown, by rotating the gears 234, 236, fluid may be pumped into the housing 204 via the inlet port 214 and flow through the inlet flow channel 228 to the gear pump. The fluid may then be directed along two separate flow paths defined between the outer perimeter of each gear 234, 236 and the inner perimeter of its corresponding gear cavity 238 before flowing into the outlet flow channel 230. As shown in FIG. 18, flow diverters 244 may be provided on each side of the gear pump to facilitate diverting the flow of fluid into the two separate flow paths. The fluid flowing into the outlet flow channel 230 may then be directed into the outlet ports 216, 218 and expelled from the housing 204.

In accordance with several aspects of the present subject matter, the driver assembly 210 may be configured to be activated or driven magnetically using the disclosed activator device 202. Specifically, in several embodiments, the drive shaft 240 may be configured to be rotatably driven by one or more drive magnets 246 positioned within the housing 204 adjacent to its outer face 248 (e.g., the outer face 248 defined by the upper housing component 222). For example, as shown in FIGS. 16 and 17, a disc-shaped drive magnet 246 may be configured to be positioned within a magnet cup 250 provided within the housing 204 so that the drive magnet 246 and the magnet cup 250 are rotatably engaged with one another. In such an embodiment, the drive shaft 240 may be formed integrally with and/or may be coupled to the magnet cup 250 and extend outwardly therefrom so as to be rotatably coupled to the drive gear 234. For instance, as shown in FIG. 17, the drive shaft 240 may be configured to extend through an opening 252 defined in an upper wall of the central housing component 226 to allow the drive shaft 240 to be rotatably coupled to the drive gear 234. As a result, rotation of both the drive magnet 246 and its corresponding magnet cup 250 may rotationally drive the drive shaft 240, which, in turn, results in rotation of the drive gear 234. Thus, by placing the activator device 202 adjacent to the location of the driver assembly 210, the activator device 202 may be used to externally drive the driver assembly 210, thereby allowing the valves 24, 26 to be easily and effectively opened and closed. For instance, in one embodiment, the activator device 202 may be placed in contact with or adjacent to the patient's skin at a location directly above the outer face 248 of the housing 204 to allow the driver assembly 210 to be magnetically driven.

It should be appreciated that, in several embodiments, the actuator assembly 200 may also include one or more suitable bearings or bearing elements to facilitate or enhance rotation of the magnet cup 250 within the housing 204. For instance, as shown in FIG. 16, an annular assembly of balls 254 may be configured to be positioned between the magnet cup 250 and the housing 204 (e.g., at the location of the upper housing component 222). In such an embodiment, the balls 254 may be vertically supported within the housing 204 via an annular flange 256 (FIGS. 16 and 17) extending outwardly from the magnet cup 250.

Referring particularly to FIGS. 12, 20 and 21, the activator device 202 may generally be configured similar to the activator device 102 described above. Specifically, in several embodiments, the activator device 202 may correspond to a small, hand-held device that includes a reversible motor 258 rotatably coupled to one or more activator magnets 260 positioned at and/or adjacent to a contact end 262 of the device 202. The activator magnet(s) 260 may, in turn, be configured to magnetically react with the drive magnet 246 provided within the housing 204, thereby allowing the gear pump to be magnetically driven in manner that allows fluid to be pumped out of and back into the fluid reservoir 212. Similar to the embodiment described above, it should be appreciated that the reversible motor 258 may be configured to rotate the activator magnet(s) 260 in both a clockwise and a counter-clockwise direction. Thus, by rotating the motor 258 in a first direction, the drive magnet 246 may be rotated in a direction that causes the drive and idler gears 234, 236 of the driver assembly 210 to be rotated in a corresponding direction for pumping fluid from the reservoir 212 to the valves 24, 26. Similarly, by rotating the motor 258 in the opposite direction, the drive magnet 246 may be rotated in a direction that causes the gears 234, 236 to be rotated in a corresponding direction for pumping fluid from the valves 24, 26 back into the reservoir 212.

In several embodiments, the activator device 202 may include one or more user interface elements to allow the operator to select the desired rotational direction of the motor 258. For instance, as shown in FIG. 20, a toggle switch 264 may be provided on the exterior of the activator device 202 that can be toggled from a neutral or off position (e.g., the position at which the motor 258 is turned off) to a forward or "inflation" position so as to cause the motor 258 to be rotated in a first direction and from the off position to a reverse or "deflation" position so as to cause the motor 258 to be rotated in the opposite direction. In addition, the activator device 202 may also include an indicator light 266 that is configured to be illuminated when the toggle switch 264 is moved from the off position to the inflation or deflation position, thereby providing an indication to the operator that the motor 258 is rotating. In such an embodiment, the indicator light 266 may, for example, be configured to be illuminated in different colors to indicate whether the motor 258 is rotated in the forward or reverse direction. For instance, the indicator light 266 may be illuminated in a green color when the motor 258 is being rotated in the forward direction and in a red color when the motor 258 is being rotated in the reverse direction. Alternatively, the activator device 202 may include multiple indicator lights for indicating the operational direction of the motor 258. For instance, in a particular embodiment, the activator device 202 may include a first indicator light for indicating that the motor 258 is rotating in the forward direction and a second indicator light for indicating that the motor 258 is rotating in the reverse direction.

It should be appreciated that, as an alternative to the toggle switch 264, the activator device 202 may include any other suitable user interface elements that allow the operator to select the desired rotational direction of the motor 258. For instance, similar to the embodiment described above with reference to FIG. 9, the activator device 202 may include separate buttons for rotating the motor 258 in the forward and reverse directions. Additionally, it should be appreciated that, as an alternative to the indicator light(s) 266, the activator device 202 may include any other suitable indicator or output means for indicating that the motor 258 is operating and/or for indicating the rotational direction of the motor 258. For example, in alternative embodiment, the activator device 202 may include a suitable display (e.g., an LCD display panel) for displaying a visual indicator associated with the operational status of the motor 258.

Referring particularly to FIG. 21, the activator device 202 may also include various internal components for facilitating operation of the device 202. For instance, as shown in FIG. 21, the activator device 202 may include a battery 268 for providing power to the various other components of the device 202. In several embodiments, the battery 268 may correspond to a rechargeable battery. In such embodiments, the activator device 202 may be configured to be placed within a suitable charging station and/or connected to a suitable power cord for recharging the battery 268.

Additionally, the activator device 202 may include a controller 270 for controlling the operation of the various other components of the device 202. In general, the controller 270 may correspond to any suitable processing unit known in the art. As such, the controller 270 may include, for example, a circuit board 276 providing one or more processors 272 and associated memory 274. As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory 274 of the controller 270 may generally comprise a memory element(s) including, but not limited to, computer readable medium (e.g., random access memory (RAM)), computer readable non-volatile medium (e.g., a flash memory) and/or other suitable memory elements. Such memory 274 may generally be configured to store suitable computer-readable instructions that, when implemented by the processor(s) 272, configure the controller 270 to perform various computer-implemented functions, such as receiving operator inputs (e.g., via the toggle switch 264), controlling the operation of the motor 258, illuminating the indicator light(s) 266 and/or the like.

Moreover, in several embodiments, the activator device 202 may also include a wireless communications device 278 for transmitting to and/or receiving wireless communications from one or more components of the actuator assembly 200. For example, in one embodiment, the wireless communications device 278 may include a suitable processor 280 (e.g., an integrated circuit) and an associated antenna 282 for transmitting and/or receiving wireless communications. In such an embodiment, the processor 280 may correspond to a processor 272 of the controller 170 or a separate processor contained within the activator device 202 (e.g., on a separate circuit board). Alternatively, the wireless communications device 278 may include any other suitable component(s) that allows wireless communications to be transmitted from and/or received by the activator device 202.

In a particular embodiment of the present subject matter, the wireless communications device 278 may be configured to serve as an initiator device for near field communications (NFC) by actively generating a radiofrequency (RF) field designed to power a corresponding communications device 284 (FIG. 15) provided within the actuator assembly 200. As will be described below, the NFC-powered communications device 284 of the actuator assembly 200 may be configured to receive sensor measurements corresponding to the pressure of the fluid contained within the system 50 and transmit such sensor measurements back to the wireless communications device 278 installed within the activator device 202. The sensor measurements received by the wireless communications device 278 may then be stored within the associated memory 274 of the controller 270 and/or wirelessly transmitted to a separate device in communication with the activator device 202. In addition, the sensor measurements may also be utilized to indicate to the operator whether the system 50 is operating properly. For instance, as will be described below, the activator device 202 may include an indicator bar 285 or other suitable output device for providing the operator with a visual indication of the inflation/deflation level of the valves 24, 26 based on the pressure measurements received by the wireless communications device 278.

Referring still FIGS. 12-21, in several embodiments, the actuator assembly 200 may also include a back-up septum 286 to provides a means for adding fluid into and/or removing fluid from the actuator assembly 200 to ensure that the proper amount of fluid is contained within the assembly 200 and/or to open/close the valves 24, 26. For example, as shown in the illustrated embodiment, the septum 286 may be positioned on the exterior of the housing 204 at a suitable location for providing access to the fluid path defined through the housing 204 (e.g., at a location adjacent to the first end 206 of the housing 204). Thus, if necessary, a hypodermic needle may be inserted into the patient's skin and through the septum 286 to add fluid to and/or remove fluid from the actuator assembly 200. For instance, if the driver assembly 210 is not operating properly, fluid may be removed from the actuator assembly 200 via the septum 286 in order to open the valves 24, 26. Similarly, additional fluid may be added to the actuator assembly 200 via the septum 286 in order to close the valves 24, 26.

It should be appreciated that, similar to the embodiment described above with reference to FIGS. 3-8, the septum 286 may be made from any suitable material capable of receiving the tip of a hypodermic needle. For example, in one embodiment, the septum 286 may be made from an elastomeric film, such as a silicone membrane.

Additionally, in several embodiments, the disclosed system 50 may also include a pressure accumulator 287 configured to assist in maintaining a constant pressure of the fluid contained within the system 50. For example, as shown in FIG. 12, in one embodiment, the pressure accumulator 287 may be provided in fluid communication with one of the valve tubes 40, 42 extending between the actuator assembly 200 and its corresponding valve 24, 26. In such an embodiment, in addition to assisting in maintaining a constant fluid pressure, the pressure accumulator 287 may also be configured to serve as a flow restrictor for the fluid being supplied through the associated valve tube 40, 42. As a result, the pressure accumulator 287 may provide a means for sequentially closing the valves 24, 26. For instance, as indicated above, it may be desirable to close the valve positioned at the arterial end of the arteriovenous graft 12 prior to closing the valve positioned at the venous end of the graft 12. In such instance, the pressure accumulator 287 may be provided in fluid communication with the valve tube configured to supply fluid to the valve positioned at the venous end of the graft 12, thereby allowing the accumulator 287 to restrict the flow of fluid to such valve. As a result, the closing of the valve positioned at the venous end of the graft 12 may be delayed by a time constant that is directly proportional to the flow restriction provided by the pressure accumulator 287 so that the valve positioned at the arterial end of the arteriovenous graft 12 is closed first.

It should be appreciated that, in alternative embodiments, the pressure accumulator 287 may be provided at any other suitable location, such as within the housing 204. Moreover, it should be appreciated that, in alternative embodiments, the system 50 may include any other suitable means for sequentially closing the valves 24, 26, such as by varying the inner diameter(s) of the outlet ports 216, 218 and/or the tubes 40, 42 connecting the outlet ports 216, 218 to the valves 24, 26.

Moreover, in accordance with aspects of the present subject matter, the disclosed system 50 may also include one or more pressure sensors 288, 289 for sensing the pressure of the fluid supplied within the system 50. For example, as particularly shown in FIG. 15, in one embodiment, the actuator assembly 200 may include two pressure sensors (e.g., a first pressure sensor 288 and a second pressure sensor 289) positioned within the housing 204 for monitoring the pressure of the fluid supplied through the housing 204. Specifically, the first pressure sensor 288 may be provided in fluid communication with the first outlet port 216 for monitoring the pressure of the fluid supplied through such port 216 when opening and closing the first valve 24. Similarly, the second pressure sensor 289 may be provided in fluid communication with the second outlet port 218 for monitoring the pressure of the fluid supplied through such port 218 when opening and closing the second valve 26. As indicated above, by monitoring the pressure of the fluid supplied to each valve 24, 26, the operator may be provided an indication of whether the associated balloons have been fully inflated/deflated as fluid is being pumped to or drawn out of each valve 24, 26, thereby allowing the operator to determine if each valve 24, 26 has been properly closed/opened.

It should be appreciated that each pressure sensor 288, 289 may generally correspond to any suitable sensor(s) configured to directly or indirectly sense the fluid pressure within the system 50. For example, in several embodiments, each pressure sensor 288, 289 may correspond to a pressure-sensitive film configured to provide an output signal(s) (e.g., a current signal(s)) indicative of the load experienced by the film due to the pressure of the fluid flowing around and/or past the sensor 288, 289. One example of a suitable pressure-sensitive film that may be utilized as a pressure sensor in accordance with aspects of the present subject matter is described in U.S. Patent Publication Number 2013/0204157 entitled "Contact Sensors, Force/Pressure Sensors and Methods for Making Same" (Clark et al) and filed on Oct. 5, 2012 (U.S. Ser. No. 13/636,345, also published as WO 2011/127306), the disclosure of which is hereby incorporated by reference herein in its entirety for all purposes.

In one particular embodiment of the present subject matter, the pressure sensors 288, 289 may correspond to a pressure sensitive film(s) that includes a partially conductive sensor material and at least one conductor encapsulated within a hermetic/moisture proof coating in order to fluidly isolate the sensor material and the conductor(s) from the fluid contained within the system 50. In such an embodiment, the sensor material may correspond to any suitable material that undergoes a detectable change (e.g., a change in material or electrical properties) in response to variations in the pressure of the fluid exposed to the sensor 288, 289. For instance, the sensor material may correspond to an electrically conductive polyimide film (e.g., KAPTON XC manufactured by DUPONT) that is configured to be positioned adjacent to the conductor(s) such that the contact area defined between the sensor material and the conductor(s) changes in response to variations in the fluid pressure due to deformation of the sensor material. Specifically, in one embodiment, the contact area may increase with increases in the pressure. Such increases in the contact area between the sensor material and the conductor(s) may result in an increase in the conductivity of the sensor 288, 289 and, thus, a decrease in the electrical resistance within the sensor 288, 289, which may then be detected and correlated to the fluid pressure within the system 50.

Figure 22:
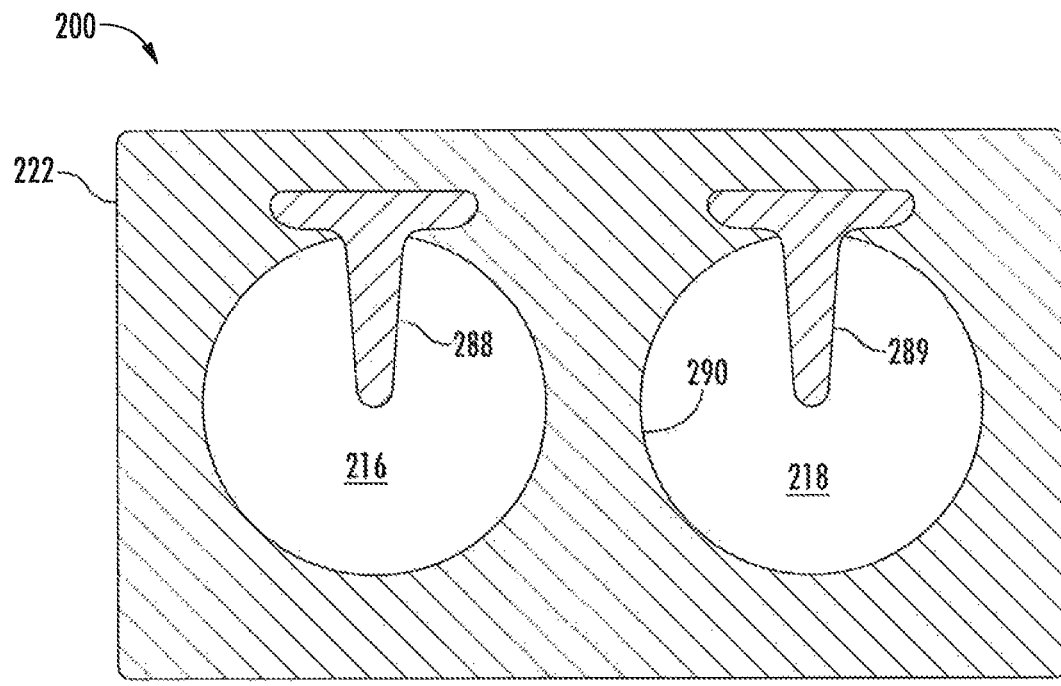
FIG. 22 illustrates a cross-sectional view of the actuator assembly shown in FIG. 15 taken about line 22,23-22,23, particularly illustrating one embodiment of a pressure sensor arrangement for sensing the pressure of the fluid supplied within the system.
Figure 23:
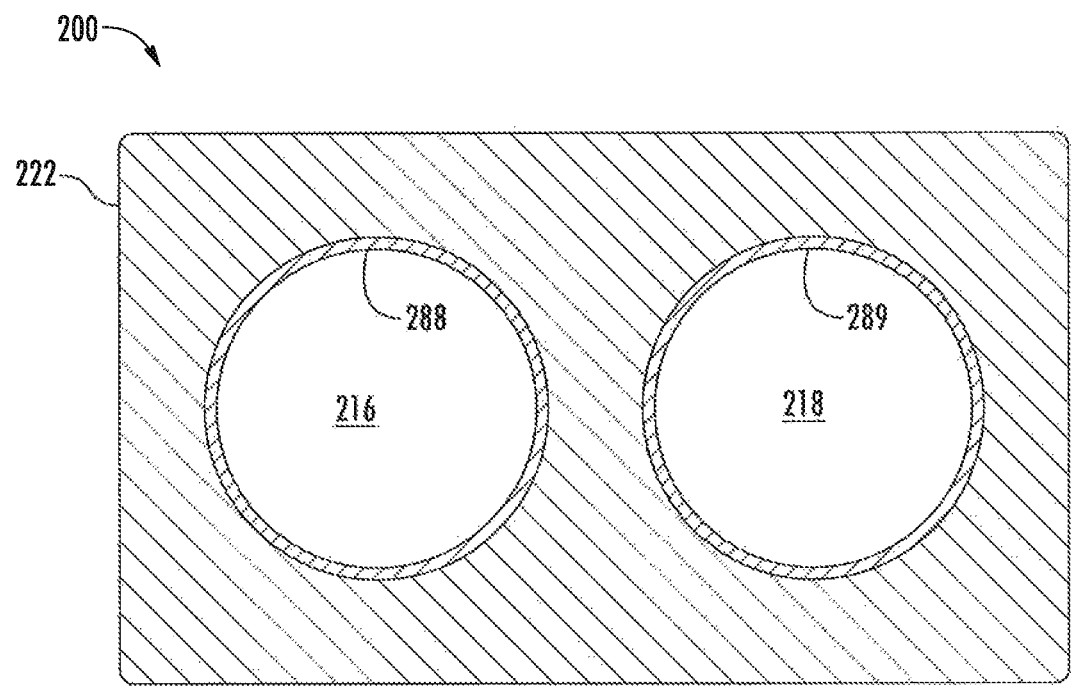
FIG. 23 illustrates another cross-sectional view of the actuator assembly shown in FIG. 15 taken about line 22,23-22,23, particularly illustrating another embodiment of a pressure sensor arrangement for sensing the pressure of the fluid supplied within the system.

In embodiments in which each pressure sensor 288, 289 corresponds to a pressure-sensitive film, it should be appreciated that the film may generally be placed at any suitable location that allows the film to directly or indirectly monitor the pressure of the fluid supplied through the system 50. For instance, in one embodiment, the pressure-sensitive film may be placed within the housing 204 such that the film extends directly into the flow path defined by each outlet port 216, 218. For instance, FIG. 22 illustrates a cross-sectional view of the housing 204 shown in FIG. 15 taken about line 22,23-22,23, particularly illustrating one example of a suitable arrangement for positioning a pressure-sensitive film within the flow path of the fluid being directed through the outlet ports 216, 218. As shown, each sensor 288, 289 may be configured to extend outwardly from an inner surface 290 of the corresponding outlet port 216, 218 such that the pressure-sensitive film is exposed to fluid along both its sides. Alternatively, the pressure-sensitive film may be positioned at any other suitable location within and/or around the flow path of the fluid through the housing 204. For example, FIG. 23 illustrates another cross-sectional view of the housing 204 shown in FIG. 15 taken about line 22,23-22,23, particularly illustrating another example of a suitable arrangement for positioning a pressure-sensitive film within the flow path of the fluid being directed through the outlet ports 216, 218. As shown, each sensor 288, 289 may be configured to extend around the inner circumference of its corresponding outlet port 216, 218 such that the fluid directed through the port 216, 218 contacts the film along its inner perimeter.

Figure 24:
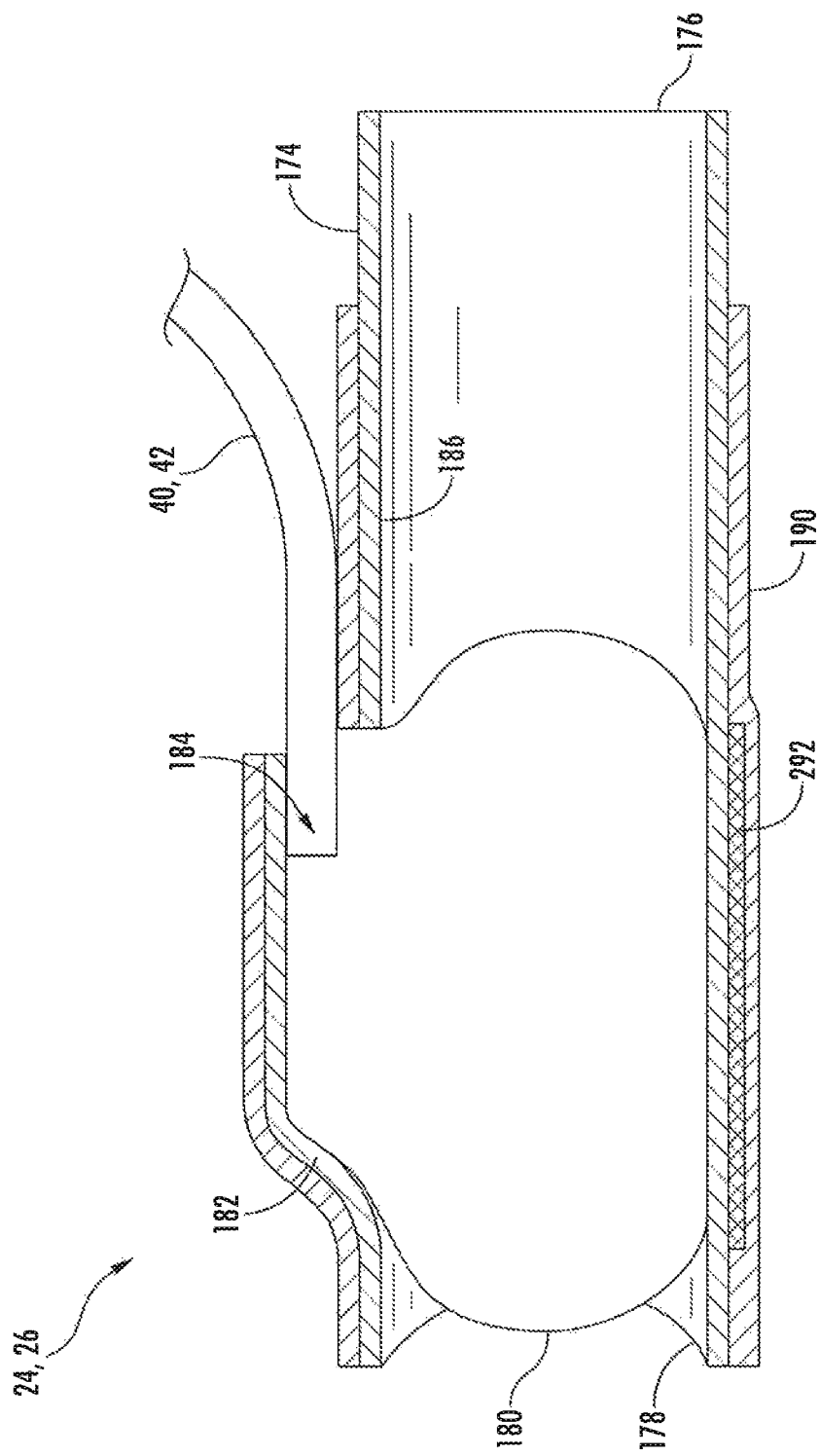
FIG. 24 illustrates a cross-sectional view of another embodiment of a fluid-actuated balloon valve suitable for use within the disclosed system, particularly illustrating the valve in a closed position and also illustrating a pressure sensor provided in operative associated with the valve.

In other embodiments, the pressure sensors 288, 289 may be disposed at any other suitable location along the fluid flow path that allows the sensors 288, 289 to monitor the pressure of the fluid within the system 50. For instance, in an alternative embodiment, a pressure sensor (indicated by dashed lines 291 in FIG. 12) may be provided in fluid communication with each valve tube 40, 42 extending between the actuator assembly 20 and one of the valves 24, 26 to allow the pressure within each valve tube 24, 26 to be monitor. In another embodiment, a pressure sensor may be provided in operative association with each valve 24, 26. For example, FIG. 24 illustrates a cross-sectional view of one embodiment of a suitable configuration for associating a pressure sensor 292 within each valve 24, 26. As shown, the valve 24, 26 may be configured similarly to the valve 24, 26 shown in FIGS. 10 and 11. For example, the valve 24, 26 may include a balloon 180 configured to be inflated (e.g., via fluid supplied thereto by the associated valve tube 40, 42) within a cylindrical housing or sleeve 174. In addition, the valve 24, 26 includes an outer sleeve 190 extending circumferentially around the inner sleeve 174 so as to surround at least a portion of the inner sleeve 174. In such an embodiment, a pressure sensor 292 (e.g., a pressure-sensitive film) may be installed between the inner and outer sleeves 174, 190 so as to extend circumferentially around at least a portion of the area along which the inner sleeve 174 will be forced outwardly due to inflation of the balloon 180. As such, when the balloon 180 is inflated and applies a radially outward force against the inner sleeve 174, the pressure sensor 292 may be configured to detect such force, thereby providing an indication of the pressure within the balloon 180.

It should be appreciated that, as an alternative to the use of pressure sensitive films, the pressure sensors 288, 289 may correspond to any other suitable sensors capable of detecting or sensing the pressure of the fluid supplied at any location within the disclosed system 50. For instance, suitable pressure sensors for use within the disclosed system 50 may include, but are not limited to, pressure sensors utilizing piezoresistive strain gauges and/or relying on capacitive, electromagnetic, piezoelectric, optical and/or potentiometric sensing techniques.

Referring back to FIGS. 21-21, as indicated above, the actuator assembly 200 may also include a sensor communications device 284 communicatively coupled to the pressure sensors 228, 289 that is configured to receive/store the sensor measurements transmitted from the sensor(s) 288, 289 and/or wirelessly transmit such sensor measurements to a separate wireless communication device positioned outside the patient's body. For example, as indicated above, the activator device 202 may include a wireless communications device 278 incorporated therein for receiving and/or transmitting wireless communications. As a result, wireless communications associated with the pressure measurements received from the pressure sensor(s) 288, 289 may be transmitted from the sensor communications device 284 to the activator device 202.

In several embodiments, the sensor communications device 284 may include a suitable processor 293 (FIG. 15) (e.g., an integrated circuit) and an associated antenna 294 (FIG. 15) for receiving and/or transmitting wireless communications. In such an embodiment, the sensor communications device 284 may be powered via an onboard battery, which may allow for data logging of the pressure sensor measurements. Alternatively, the sensor communications device 284 may be configured, to be remotely powered, thereby eliminating the requirement for a battery to be placed within the implanted actuator assembly 200. For instance, as described above, the sensor communications device 284 may be configured to be powered via, a radio frequency (RF) field generated by the NFC-equipped wireless communications device 278 of the activator device 202. In such instance, while power is being provided to the processor 293 via the electromagnetic field generated by the wireless communication device 278, the sensor communications device 284 may receive sensor measurements from the pressure sensors 288, 289 and cause such measurements to be transmitted wirelessly via the antenna 294. As a result, the NFC powered communications device 284 may allow for instantaneous or real time pressure measurements associated with the current fluid pressure within the system 50 to be transmitted wirelessly to the activator device 202 (or any other suitable device positioned exterior to the patient).

It should be appreciated that the antenna 294 associated with the sensor communications device 284 may generally be configured to provide wireless communications via any suitable wireless communications protocol. For instance, in one embodiment, the antenna 294 may allow for NEC-based communications to be transmitted from the sensor communications device 284. Alternatively, any other suitable wireless communications protocol may be utilized, such as Bluetooth and/or the like.

As indicated above, when the activator device 202 is placed in contact with or adjacent to the patient's skin at a location directly above the actuator assembly 200 in order to magnetically drive the driver assembly 210, the wireless communication device 278 of the activator device 202 may also be used to simultaneously generate an electromagnetic field that is capable of powering the sensor communications device 284. Thus, as the valves 24, 26 are being inflated via magnetic activation of the driver assembly 210, the NFC-powered sensor communication device 284 may be configured to receive instantaneous pressure measurements from the pressure sensor(s) 288, 289 and transmit such measurements to the wireless communication device 278. As indicated above, the pressure measurements received by the wireless communications device 278 may then be utilized to provide the operator with a visual indication of the inflation/deflation level of the valves 24, 26.

For example, as shown in FIG. 20, the activator device 202 may include an indicator bar 285 including a plurality of lights 295 configured to be sequentially illuminated as the fluid pressure within the system 50 increases. As a result, the indicator bar 285 may provide an indication of the inflation/deflation level of the balloon valves 24, 26. For instance, the controller 270 of the activator device 202 may be configured to illuminate all of the lights 295 contained within the indicator bar 285 when the monitored fluid pressure indicates that the balloon valves 24, 26 are fully inflated and turn off all of the lights 295 when the monitored fluid pressure indicates that the balloon valves 24, 26 are fully deflated. Thus, as the operator is using the activator device 202 to inflate the balloons (i.e., to close the valves 24, 26), he/she may view the indicator bar 285 as additional lights 295 contained within the indicator bar 285 are illuminated with increases in the fluid pressure. When all of the lights 295 have been illuminated (thereby indicating that the balloons are fully inflated), the operator may turn off the activator device 202 or otherwise move the device away from the patient. Similarly, when the operator is using the activator device 202 to deflate the balloons (i.e., to open the valves 24, 26), he/she may view the indicator bar 285 as the lights 295 are sequentially turned off. When all of the lights 295 have been turned off (thereby indicating that the balloons are fully deflated), the operator may turn off the activator device 202 or otherwise move the device away from the patient.

It should be appreciated that, in alternative embodiments, the activator device 202 may include any other suitable means for providing the operator with an indication of the inflation/deflation level of the balloon valves 24, 26. For example, in one embodiment, the activator device 202 may incorporate a display panel (e.g., an LCD display panel) that may be used to display alphanumeric data, graphs and/or any other suitable data that provides the operator with a visual indication of the inflation/deflation level of the valves 24, 26. In addition to visual indicators (or as an alternative thereto), the activator device 202 may also include one or more speakers for providing an audible indication of the inflation/deflation level of the valves 24, 26.

Moreover, in one embodiment, the controller 270 may be configured automatically control the operation of the activator device 202 based on the pressure measurements received from the pressure sensors 288, 289. For example, the controller 270 may be configured to automatically turn off the motor 258 when the pressure measurements received from the pressure sensors 288, 289 indicate that the valves 24, 26 have been fully deflated (i.e., when opening the valves 24, 26 to begin the hemodialysis process) and/or fully inflated (i.e., when closing the valves 24, 26 to complete the hemodialysis process).

Figure 25:
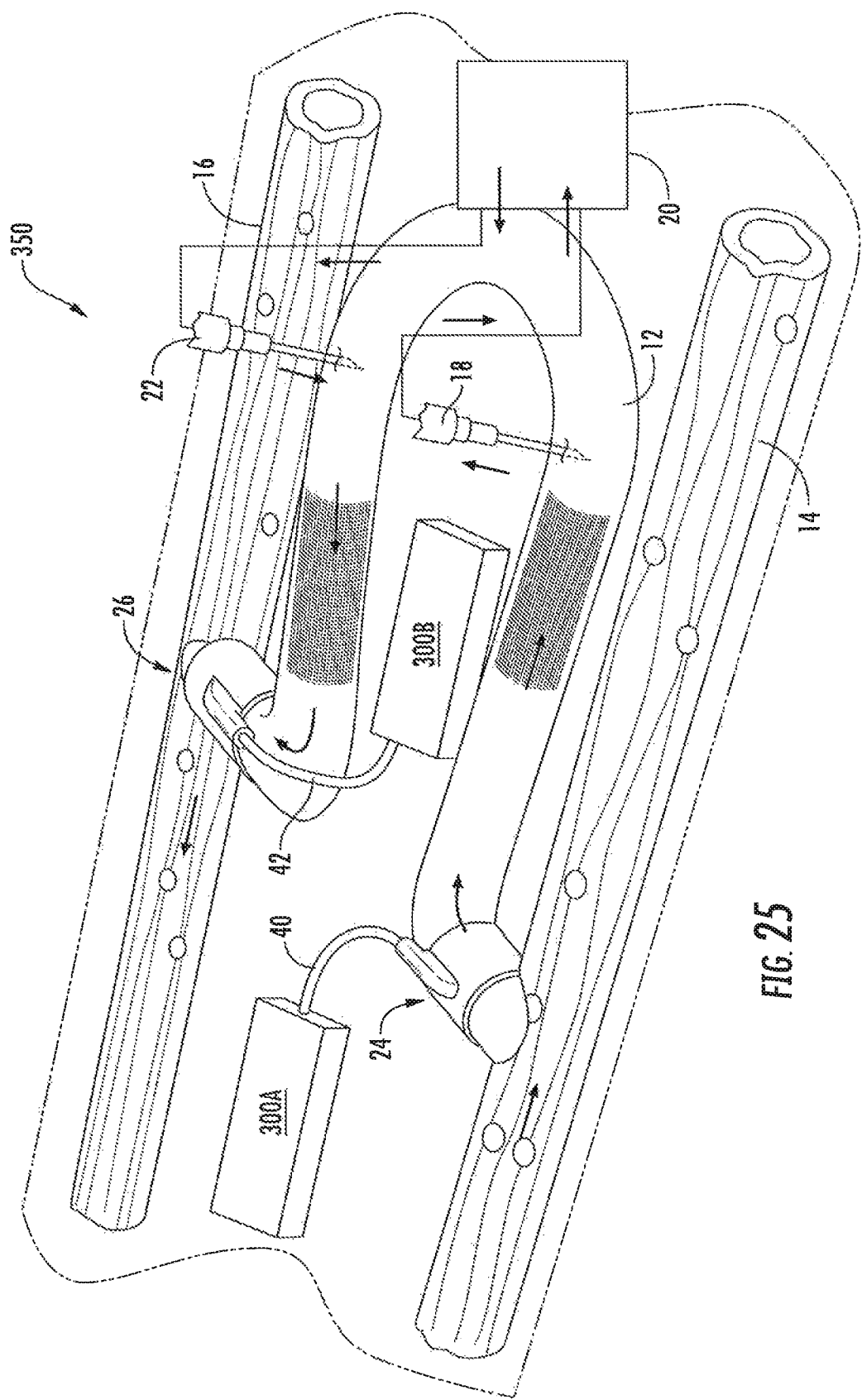
FIG. 25 illustrates a simplified, perspective view of another embodiment of arteriovenous access valve system in accordance with aspects of the present subject matter.

Referring now to FIG. 25, another embodiment of an arteriovenous access valve system 350 is illustrated in accordance with aspects of the present subject matter. As shown, the system 350 may generally be configured similar to the system 50 described above with reference to FIG. 2. For instance, the system 350 may include an arteriovenous graft 12 coupled between an artery 14 and a vein 16. In order to carry out hemodialysis, a first hypodermic needle 18 is inserted through the skin and into the arteriovenous graft 12. Blood is removed from the arteriovenous graft 12 through the needle and into a dialysis machine 20. In the dialysis machine, waste materials are removed from the blood. After circulating through the dialysis machine 20, the blood is then fed back into the arteriovenous graft 12 through a second hypodermic needle 22.

In addition, the system 350 may include a first valve 24 positioned at or adjacent to the arterial end of the arteriovenous graft 12 and a second valve 26 positioned at or adjacent to the venous end of the arteriovenous graft. As indicated above, in several embodiments, the valves 24, 26 may correspond to balloon-actuated valves and, thus, may each include an inflatable balloon (not shown). When inflated, the balloons close the valves 24, 26 in a manner that reduces or eliminates the blood flow through the graft 12. In contrast, when the balloons are deflated, the valves 24, 26 are opened and blood may be directed through the arteriovenous graft 12.

However, unlike the system 50 described above, each valve 24, 26 may be configured to be in fluid communication with a separate actuator assembly 300A, 300B for inflating/deflating its corresponding balloon. Specifically, as shown in the illustrated embodiment, the system 350 may include a first actuator assembly 300A in fluid communication with the first valve 24 (e.g., via a first valve tube 40). Additionally, the system 350 may include a second actuator assembly 300B in fluid communication with the second valve 26 (e.g., via a second valve tube 42). By providing a separate actuator assembly 300A, 300B in operative association with each valve 24, 26, the valves 24, 26 may be opened and closed independently. For example, when the hemodialysis process is completed, the valve positioned at the arterial end of the arteriovenous graft 12 (e.g., the first valve 24) may be initially closed by activating the first actuator assembly 300A. Thereafter, the valve positioned at the venous end of the graft 12 (e.g., the second valve 26) may be closed by separately activating the second actuator assembly 300A.

It should be appreciated that, in several embodiments, the actuator assemblies 300A, 300B may correspond to magnetically activated actuator assemblies. For instance, in one embodiment, each actuator assembly 300A, 300B may be configured the same as or similar to the actuator assembly 100 described above with reference to FIGS. 3-8 and/or the actuator assembly 200 described above with reference to FIGS. 12-19.

It should also be appreciated that, in alternative embodiments, the system 350 may include any other suitable means for independently opening and closing the valves 24, 26. For instance, as an alternative to including two separate actuator assemblies, the system 350 may include a single actuator assembly configured to independently open and close each valve 24, 26. In such an embodiment, the actuator assembly may, for example, include two separate screw/plunger drives and/or two separate gear pumps housed therein for independently supplying fluid into and drawing fluid out of each valve 24, 26. Alternatively, the single actuator assembly may include a flow diverter (e.g., a directional flow valve or other similar type of mechanism) that allows the flow of fluid to be diverted to each valve 24, 26 separately or to both valves 24, 26 in combination.

Figure 26:
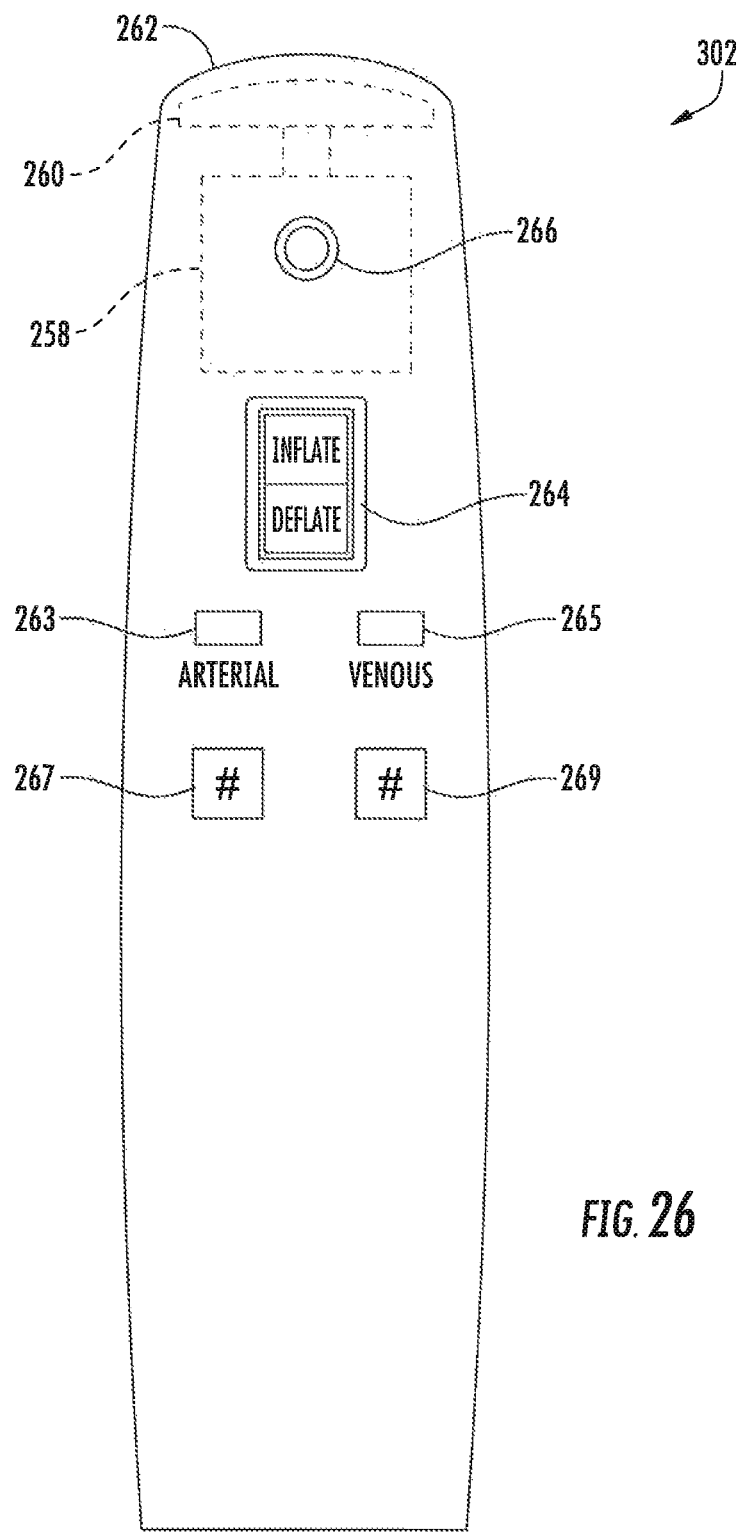
FIG. 26 illustrates a side view one embodiment of an activator device that may be utilized on connection with the system shown in FIG. 25.

Referring now to FIG. 26, a front view of one embodiment of an activator device 302 that may be utilized in association with the system 350 in order to independently activate the valves 24, 26 is illustrated in accordance with aspects of the present subject matter. In general, the activator device 302 may be configured the same as or similar to the activator device 202 described above with reference to FIGS. 12, 20 and 21. For example, as shown, the activator device 302 may include a reversible motor 258 rotatably coupled to one or more activator magnets 260 positioned at and/or adjacent to a contact end 262 of the device 302. Similar to the embodiments described above, the activator magnet(s) 260 may, in turn, be configured to magnetically react with the drive magnet of each actuator assembly 300A, 300B to allow fluid to be transported to and drawn back out of its corresponding valve 24, 26. In addition, the activator device 302 may include one or more internal components (not shown) for facilitating desired operation of the device 302, such as a battery (e.g., the battery 268 shown in FIG. 21), a controller (e.g., the controller 270 shown in FIG. 21), a wireless communications device (e.g., the wireless communications device 278 shown in FIG. 21) and/or any other suitable internal components.

Moreover, similar to the activator device 202 described above, a toggle switch 264 may be provided on the exterior of the activator device 302 that can be toggled from a neutral or off position (e.g., the position at which the motor 258 is turned off) to a forward or "inflation" position so as to cause the motor 258 to be rotated in a first direction and from the off position to a reverse or "deflation" position so as to cause the motor 258 to be rotated in the opposite direction. Additionally, the activator device 302 may also include an indicator light 266 that is configured to be illuminated in one or more colors when the toggle switch 264 is moved from the off position to the inflation or deflation position, thereby providing an indication of the operational status and/or rotational direction the motor 258.

As shown in FIG. 26, unlike the embodiment described above with reference to FIGS. 12, 20 and 21, the activator device 302 may also include valve indicator lights 263, 265 for providing the operator with an indication of which actuator assembly 300A, 300B can be currently controlled by the activator device 302. Specifically, as shown in the illustrated embodiment, the activator device 302 may include a first valve indicator light 263 that is configured to be illuminated when the activator device 302 is placed adjacent to the first actuator assembly 300A (e.g., by placing the activator device 302 in contact with or adjacent to the patient's skin at a location directly above the location of the actuator assembly 300A). Similarly, the activator device 302 may include a second valve indicator light 265 that is configured to be illuminated when the activator device 302 is placed adjacent to the second actuator assembly 300B (e.g., by placing the activator device 302 in contact with or adjacent to the patient's skin at a location directly above the location of the actuator assembly 300B). As such, when the first valve indicator light 263 is illuminated, the operator may be provided with an indication that the activator device 302 is properly positioned for activating the first actuator assembly 300A, thereby allowing the first valve 24 to be opened and/or closed. Similarly, when the second valve indicator light 265 is illuminated, the operator may be provided with an indication that the activator device 302 is properly positioned for activating the second actuator assembly 300A, thereby allowing the second valve 26 to be opened and/or closed.

It should be appreciated that the valve indicator lights 263, 265 may be triggered using any suitable means known in the art. For instance, in one embodiment, the appropriate valve indicator light 263, 265 may be illuminated when the activator device 302 is placed sufficiently close to one of the actuator assemblies 300A, 300B to allow an NFC-based connection to be established between the device 302 and such actuator assembly 300A, 300B. Specifically, in embodiments in which the actuator assemblies 300A, 300B are configured the same as or similar to the actuator assembly 200 described above, the activator device 302 may be configured to illuminate the valve indicator light 263, 265 corresponding to the actuator assembly 300A, 300B from which pressure measurements are currently being received, thereby indicating that the activator device 302 has been placed close enough to the actuator assembly 300A, 300B in order to power its on-board sensor communications device 284 (FIG. 15) via NFC. For instance, when the activator device 302 is placed adjacent to the first actuator assembly 300A, the proximity of the two components may allow the on-board sensor communications device 284 of the first actuator assembly 300A to be powered and begin to wirelessly transmit pressure measurements to the activator device 302. Upon receipt of the initial pressure measurements, the activator device 302 may then illuminate the first valve indicator light 263 to indicate to the operator that the activator device 302 may be used to open and/or close the first valve 24.

Additionally, the activator device 302 may also include a suitable means for providing the operator with an indication of the inflation/deflation level of each valve 24, 26. For instance, as shown in FIG. 26, the activator device 302 may include a first display panel 267 for providing an indication of the inflation/deflation level of the first valve 24 and a second display panel 269 for providing an indication of the inflation/deflation level of the second valve 26. By including such display panels 267, 269, the inflation/deflation levels of the valves 24, 26 may be displayed to the operator separately, thereby allowing the operator to cheek the individual status of each valve 24, 26 as its corresponding actuator assembly 300A, 300B is being activated.

It should be appreciated that the display panels 267, 269 may generally correspond to any suitable display panel or device that allows alphanumeric characters, images and/or any other suitable displayable items to be presented to the operator. For instance, in one embodiment, the display panels 267, 269 may correspond to LCD display panels that allow graphs, symbols, images and/or the like to be displayed to the operator. Alternatively, each display panel 267, 269 may correspond to a device that is simply configured to display a digital readout (e.g., numerical values) corresponding to the inflation/deflation level of each valve 24, 26.

It should also be appreciated that, as an alternative to the display panels 267, 269, the activator device 302 may include any other suitable means for providing the operator with an indication of the inflation/deflation level of each valve 24, 26. For instance, similar to the embodiment described above with reference to FIG. 20, the activator device 302 may include two separate pressure indicator bars, with each indicator bar including a plurality of lights configured to be illuminated so as to provide a visual indication of the inflation/deflation level of its associated valve 24, 26.

Figure 27:
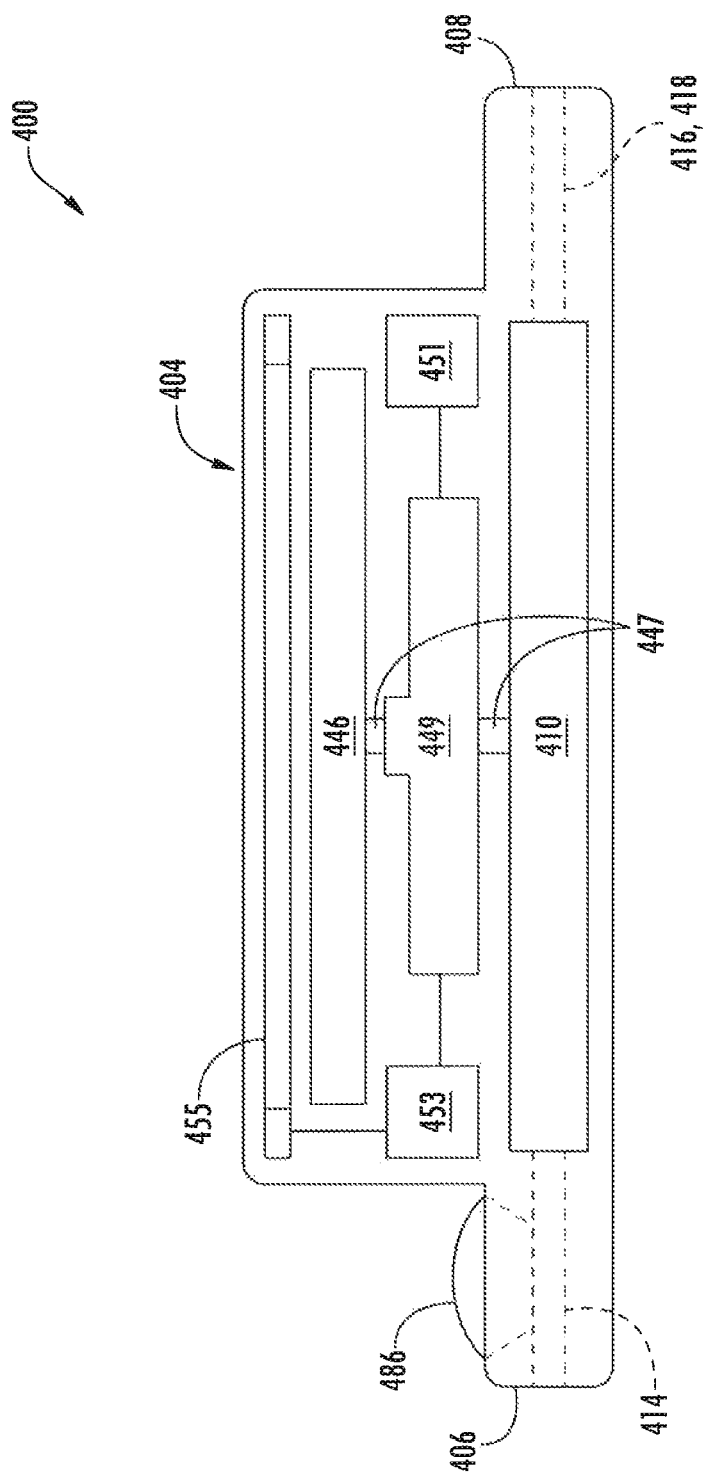
FIG. 27 illustrates a schematic view of another embodiment of an actuator assembly that may be utilized in accordance with aspects of the present subject matter, particularly illustrating the actuator assembly including various drive options.

Referring now to FIG. 27, a schematic view of another embodiment of an actuator assembly 400 that may be utilized within any of the arteriovenous access valve systems 50, 350 described herein is illustrated in accordance with aspects of the present subject matter. As will be described below, the illustrated actuator assembly 400 includes various different means for rotationally driving its associated driver assembly 410, thereby allowing fluid to be supplied to and/or drawn back out of the valves 24, 26 provided in fluid communication with the assembly 400.

In general, the actuator assembly 400 may be configured similar to the actuator assembly 200 described above with reference to FIGS. 12-19. For example, the actuator assembly 400 may include both a housing 404 extending lengthwise between a first end 406 and a second end 408 and a driver assembly 410 located within the housing 404 between its first and second ends 406, 410. Similar to the embodiment described above, the driver assembly 410 may generally correspond to a gear pump that, when activated, may be configured to pump or transport a suitable fluid (e.g., a saline solution) between a fluid reservoir (not shown) and corresponding valves 24, 26 fluidly connected to the actuator assembly 400. Additionally, as shown in the illustrated embodiment, the actuator assembly 400 may include an inlet port 414 defined by and/or through a portion of the housing 404 (e.g., at the first end 406 of the housing 404) and one or more outlet ports 416, 418 defined by and/or through a different portion of the housing 404 (e.g., at the second end 408 of the housing 204). Moreover, as shown in FIG. 27, the actuator assembly 400 may also include a back-up septum 486 (e.g., positioned at the first end 406 of the housing 404) so as to provide a means for adding fluid into and/or removing fluid from the actuator assembly 400.

In several embodiments, the driver assembly 410 may be configured to be rotatably driven using one or more drive means associated with the actuator assembly 400. For example, similar to the embodiment described above with reference to FIGS. 12-19, the driver assembly 410 may be configured to be rotatably driven via a drive magnet 446 located within the housing 404. Specifically, as shown in FIG. 27, the drive magnet 446 may be rotatably coupled to the driver assembly 410 via one or more drive shafts 447. As such, when a rotating magnet is placed adjacent to the actuator assembly 400 (e.g., the activator magnet 260 of the activator device 202 shown in FIG. 12), the drive magnet 446 may be rotated therewith, thereby rotationally driving the driver assembly 410 and allowing fluid to be pumped out of the housing 404 (e.g., via the outlets 416, 418) and supplied to the associated valves 24, 26 or pumped back into the housing 404.

Additionally, as shown in FIG. 27, the actuator assembly 400 may also include a motor 449 rotatably coupled to the driver assembly 410, such as by rotatably coupling the motor 449 between the drive magnet 446 and the driver assembly 410 via the drive shaft(s) 447. In general, the motor 449 may be configured to serve as an additional drive means for the driver assembly 410. Specifically, as an alternative to the rotationally driving the drive magnet 446 via an external magnet, the motor 449 may be operated to allow the driver assembly 410 to be rotationally driven.

To allow for control of the operation of the motor 449, the actuator assembly 400 may also include a suitable controller 453 positioned within the housing 404. In several embodiments, the controller 453 may be configured to control the operation of the motor 449 based on wireless control signals received from an external device (e.g., the activator device 202). For instance, as shown in FIG. 27, the controller 453 may be communicatively coupled to a suitable antenna 455 for receiving wireless control signals. In such instance, if a wireless control signal is received by the controller 453 that indicates that the valves 24, 26 are to be closed, the controller 453 may be configured to control the motor 449 so that it is rotated in the appropriate direction for pumping fluid to the valves 24, 26. Similarly, if a wireless control signal is received by the controller 453 that indicates that the valves 24, 26 are to be opened, the controller 453 may be configured to control the motor 449 so that it is rotated in the opposite direction for pumping fluid out of the valves 24, 26.

As shown in FIG. 27, in one embodiment, power may be supplied to the motor 449 via an on-board battery 451. In such an embodiment, the battery 451 may correspond to a rechargeable battery to allow the battery 451 to be recharged when the driver assembly 410 is being rotatable driven via the drive magnet 446. Specifically, when the drive magnet 446 is being rotated using an external magnet drive, the motor 449 may serve as a generator for producing electricity for recharging the battery 451.

In addition to powering the motor 449 via the battery 451 for as an alternative thereto), the motor 449 may be configured to be powered indirectly via a remote power source. For example, similar to the sensor communications device 284 described above, the controller 453 may be configured to be powered via a remote NFC-equipped device (e.g., the activator device 202). In such instance, the NFC-powered controller 453 may be configured to supply a sufficient amount of power to the motor 449 to allow the motor 449 to rotationally drive the driver assembly 410.

It should be appreciated that various embodiments of components configured for use within an arteriovenous access valve system 50, 350 have been described herein in accordance with aspects of the present subject matter. In this regard, one of ordinary skill in the art should readily appreciate that various different combinations of system components may be utilized within any given system configuration. For example, the pressure sensors 288, 289 may also be utilized within the system. 50 described above with reference to FIGS. 3-9. For instance, the pressure sensors 288, 289 may be installed within the housing 104 of the actuator assembly 100 (e.g., at or adjacent to the outlet ports 118, 120) and/or may be provided in operative association with the valve tubes 40, 42 and/or corresponding valves 24, 26. In such an embodiment, the actuator assembly 100 may also include a sensor communications device for wirelessly transmitting the pressure measurements received from the sensors 288, 289 to a separate device located exterior to the patient. For instance, similar to the activator device 202 shown in FIGS. 12, 20 and 21, the activator device 102 may include a wireless communications device for receiving pressure measurements from the implanted actuator assembly 100.

Additionally, as indicated above, it should be appreciated that the present subject matter is also directed to a method for operating an arteriovenous access valve system 50, 350. For example, in one embodiment, the method may include positioning an external activator device 102, 202, 302 in proximity to an implanted actuator assembly 100, 200, 300A, 300B, 400 of the system and rotating a magnet of the activator device 102, 202, 302 while the activator device 102, 202, 302 is positioned adjacent to the implanted actuator assembly 100, 200, 300A, 300B, 400 so as to rotationally drive a driver assembly 110, 210, 410 of the implanted actuator assembly 100, 200, 300A, 300B, 400 and moving the activator device 102, 202, 302 away from the implanted actuator assembly 100, 200, 300A, 300B, 400 after the driver assembly 110, 210, 410 has been rotatably driven for a period of time. For instance, the driver assembly 110, 210, 410 may be rotatably driven for a period of time corresponding to the time required to open and/or close the associated valve(s) 24, 26.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. An arteriovenous access valve system, comprising:
a first valve configured to be positioned at or adjacent to an end of an arteriovenous graft;
a second valve configured to be positioned at or adjacent to an opposite end of the arteriovenous graft;
an actuator assembly in fluid communication with the first and second valves, the actuator assembly including a housing and a driver assembly positioned within the housing, the actuator assembly further including a drive magnet positioned within the housing, the drive magnet being rotatably coupled to the driver assembly such that, when the drive magnet is rotated, the driver assembly is configured to be rotatably driven so as to supply fluid to the first and second valves or to draw fluid out of the first and second valves depending on a rotational direction of the driver assembly.

2. The system of claim 1, further comprising an activator device including at least one rotatable activator magnet, the activator device being configured to be placed adjacent to the actuator assembly such that, when the activator magnet is rotated, a magnetic force between the drive magnet and the activator magnet causes the drive magnet to be correspondingly rotated so as to rotatably drive the driver assembly.

3. The system of claim 2, wherein the activator device further comprises a reversible motor rotatably coupled to the activator magnet, wherein, when the reversible motor is rotated in a first direction, the driver assembly is rotatably driven so as to supply fluid to the first and second valves and, when the reversible motor is rotated in a second opposite direction, the driver assembly is rotatably driven so as to draw fluid out of the first and second valves.

4. The system of claim 1, wherein the driver assembly includes first and second gears rotatably coupled to the drive magnet, the first and second gears being configured to mesh with one another so as to pump the fluid into or draw the fluid out of the first and second valves depending on the rotational direction of the driver assembly.

5. The system of claim 1, wherein the driver assembly includes a threaded member rotatably coupled to the drive magnet, the threaded member being coupled to a plunger configured to push the fluid into or draw the fluid out of the first and second valves depending on the rotational direction of the driver assembly.

6. The system of claim 1, wherein the housing includes a first outlet port and a second outlet port, further comprising a first valve tube connected between the first outlet port and the first valve and a second valve tube connected between the second outlet port and the second valve.

7. The system of claim 1, wherein the housing includes an inlet port in fluid communication with a separate fluid reservoir, the fluid reservoir being configured to receive at least a portion of the fluid when the fluid is drawn out of the first and second valves.

8. The system of claim 1, wherein the housing defines a fluid chamber configured to receive at least a portion of the fluid when the fluid is drawn out of the first and second valves.

9. The system of claim 1, further comprising a septum located at least partially on an exterior of the housing.

10. The system of claim 1, further comprising at least one pressure sensor configured to monitor a pressure of the fluid supplied between the actuator assembly and the first and second valves.

11. The system of claim 10, wherein the actuator assembly includes a sensor communications device communicatively coupled to the at least one pressure sensor, the sensor communications device being configured to wirelessly transmit pressure measurements provided by the at least one pressure sensor to a separate communications device.

12. An arteriovenous access valve system, comprising:
a first valve configured to be positioned at or adjacent to an end of an arteriovenous graft;
a second valve configured to be positioned at or adjacent to an opposite end of the arteriovenous graft;
an actuator assembly in fluid communication with the first and second valves, the actuator assembly including a housing and a driver assembly positioned within the housing; and
an activator device including an activator magnet, the activator device being configured to rotate the activator magnet so as to rotationally drive the driver assembly, wherein the driver assembly is configured to supply fluid to the first and second valves or draw fluid out of the first and second valves depending on a rotational direction at which the driver assembly is being driven.

13. The system of claim 12, wherein the activator device further comprises a reversible motor rotatably coupled to the activator magnet, wherein, when the reversible motor is rotated in a first direction, the driver assembly is rotatably driven so as to supply fluid to the first and second valves and, when the reversible motor is rotated in a second opposite direction, the driver assembly is rotatably driven so as to draw fluid out of the first and second valves.

14. The system of claim 12, further comprising at least one pressure sensor configured to monitor a pressure of the fluid supplied between the actuator assembly and the first and second valves, wherein the actuator assembly includes a sensor communications device communicatively coupled to the at least one pressure sensor, the sensor communications device being configured to wirelessly transmit pressure measurements provided by the at least one pressure sensor to a wireless communications device of the activator device.

15. A method for operating an arteriovenous access valve system, the arteriovenous access valve system including an implemented actuator assembly in fluid communication with first and second valves, the method comprising:
positioning an external activator device in proximity to the implanted actuator assembly, the external activator device including a rotatable magnet; and
rotating the magnet while the external activator device is positioned adjacent to the implanted actuator assembly so as to rotationally drive a driver assembly of the implanted actuator assembly, the driver assembly being configured to supply fluid to the first and second valves or draw fluid out of the first and second valves depending on a rotational direction at which the driver assembly is being driven.

16. The method of claim 15, wherein positioning the external activator device in proximity to the implanted actuator assembly comprises positioning the external activator device in contact with or adjacent to a patient's skin at a location in proximity to an implant location of the implanted actuator assembly.

17. The method of claim 15, wherein rotating the magnet while the external activator device is positioned adjacent to the implanted actuator assembly comprises rotating the magnet in a first direction while the external activator device is positioned adjacent to the implanted actuator assembly so as to rotationally drive the driver assembly in a manner that supplies fluid to the first and second valves or rotating the magnet in a second direction while the external activator device is positioned adjacent to the implanted actuator assembly so as to rotationally drive the driver assembly in a manner that draws fluid from the first and second valves.

18. The method of claim 15, further comprising monitoring a pressure of the fluid supplied between the actuator assembly and the first and second valves while the driver assembly is being rotatably driven.

19. The method of claim 15, further comprising moving the external activator device away from the implanted actuator assembly after the driver assembly has been rotatably driven for a period time sufficient to open or close the first and second valves.

* * * * *